(12) United States Patent
　　Rothschild

(10) Patent No.: US 12,685,498 B2
(45) Date of Patent: Jul. 21, 2026

(54) X-RAY DETECTION STRUCTURE AND SYSTEM

(71) Applicant: Viken Detection Corporation, Burlington, MA (US)

(72) Inventor: Peter J. Rothschild, Newton, MA (US)

(73) Assignee: VIKEN DETECTION CORPORATION, Burlington, MA (US)

( * ) Notice: Subject to any disclaimer, the term of this patent is extended or adjusted under 35 U.S.C. 154(b) by 17 days.

(21) Appl. No.: 18/042,041

(22) PCT Filed: Aug. 20, 2021

(86) PCT No.: PCT/US2021/047030
§ 371 (c)(1),
(2) Date: Feb. 17, 2023

(87) PCT Pub. No.: WO2022/040609
PCT Pub. Date: Feb. 24, 2022

(65) Prior Publication Data

US 2023/0380781 A1　　Nov. 30, 2023

Related U.S. Application Data

(60) Provisional application No. 63/068,933, filed on Aug. 21, 2020, provisional application No. 63/215,406, filed on Jun. 25, 2021.

(51) Int. Cl.
*A61B 6/00* (2024.01)
*A61B 6/40* (2024.01)
(Continued)

(52) U.S. Cl.
CPC ............ *A61B 6/4035* (2013.01); *A61B 6/584* (2013.01); *A61B 6/027* (2013.01); *A61B 6/4064* (2013.01)

(58) Field of Classification Search
None
See application file for complete search history.

(56) References Cited

U.S. PATENT DOCUMENTS 6,078,052 A　*　6/2000　DiFilippo ............... G01T 1/202
　　　　　　　　　　　　　　　　　　250/367
9,194,960 B2　　11/2015　Gagnon et al.
(Continued)

FOREIGN PATENT DOCUMENTS

CN　　　　105242349 A　　1/2016
CN　　　　106405625 A　　2/2017
(Continued)

OTHER PUBLICATIONS

European Patent Office, International Search Report and Written Opinion for PCT application No. PCT/US2021/047030, dated Jan. 11, 2022, 25 pages.
(Continued)

*Primary Examiner* — Marcus H Taningco
(74) *Attorney, Agent, or Firm* — Merchant & Gould P.C.

(57) ABSTRACT

A system for detecting a scanning beam of x-rays includes one or more scintillator volumes oriented along an x-ray scan axis. The scintillator volume(s) receive x-rays transmitted through a target and produce scintillation photons responsively. Two or more ribbons of wavelength-shifting fibers (WSFs) are optically coupled to the scintillator volume(s) along the axis via a spatial periodic adjacency of the ribbons to the axis. The ribbons receive scintillation photons from the scintillator volume(s) via the spatial periodic adjacency as the x-ray beam scans over the scan axis. At least one respective photodetector coupled to an end of each respective ribbon detects the scintillation photons carried by the respective ribbon produces a respective signal. A signal combiner selectively combines signals from one or more ribbons, for beam positions along the scan axis, to create a
(Continued)

combined signal representing a scan of the target. The scan can have enhanced spatial resolution.

22 Claims, 15 Drawing Sheets

(51) Int. Cl.
*A61B 6/58* (2024.01)
*A61B 6/02* (2006.01)

(56) References Cited

U.S. PATENT DOCUMENTS

| | | | |
|---|---|---|---|
| 9,285,488 B2 | 3/2016 | Arodzero et al. | |
| 9,658,343 B2 | 5/2017 | Arodzero et al. | |
| 9,702,984 B1 | 7/2017 | Dowell et al. | |
| 10,209,372 B2 | 2/2019 | Arodzero et al. | |
| 10,670,740 B2 | 6/2020 | Couture et al. | |
| 11,525,930 B2 | 12/2022 | Couture et al. | |
| 11,579,327 B2 | 2/2023 | Couture et al. | |
| 2002/0117625 A1 | 8/2002 | Pandelisev | |
| 2005/0023479 A1 | 2/2005 | Grodzins | |
| 2006/0231766 A1 | 10/2006 | Kolln | |
| 2007/0278413 A1 | 12/2007 | Katagiri et al. | |
| 2008/0061243 A1 | 3/2008 | Doshi et al. | |
| 2008/0315106 A1 | 12/2008 | Buchinsky | |
| 2009/0086907 A1 | 4/2009 | Smith | |
| 2010/0270462 A1 | 10/2010 | Nelson et al. | |
| 2013/0208857 A1 | 8/2013 | Arodzero et al. | |
| 2015/0097122 A1 | 4/2015 | Nakamura et al. | |
| 2017/0358380 A1* | 12/2017 | Rothschild | G01V 5/224 |
| 2018/0275289 A1 | 9/2018 | Jacobs et al. | |
| 2019/0293810 A1 | 9/2019 | Couture | |
| 2019/0391280 A1 | 12/2019 | Couture et al. | |
| 2023/0221457 A1 | 7/2023 | Couture et al. | |

FOREIGN PATENT DOCUMENTS

| | | | |
|---|---|---|---|
| CN | 104407372 B | 6/2017 | |
| CN | 113960651 A | 1/2022 | |
| CN | 116224414 A | 6/2023 | |
| CN | 116859439 A | 10/2023 | |
| DE | 19730258 A | 1/1999 | |
| EP | 0899588 A2 | 3/1999 | |
| EP | 0813692 B1 | 8/2002 | |
| JP | 58-75083 A | 5/1983 | |
| JP | 61-68580 A | 4/1986 | |
| JP | 62-193580 U | 12/1987 | |
| JP | 2-16080 U | 2/1990 | |
| JP | 3-48188 A | 3/1991 | |
| JP | H03 242590 A | 10/1991 | |
| JP | 6-109848 A | 4/1994 | |
| JP | 6-214035 A | 8/1994 | |
| JP | 9-159769 A | 6/1997 | |
| JP | 10-186034 A | 7/1998 | |
| JP | 10-232284 A | 9/1998 | |
| JP | 10-307184 A | 11/1998 | |
| JP | 11-160437 A | 6/1999 | |
| JP | 11-211836 A | 8/1999 | |
| JP | 11-352235 A | 12/1999 | |
| JP | 2000-65937 A | 3/2000 | |
| JP | 2000-147125 A | 5/2000 | |
| JP | 2000-304864 A | 11/2000 | |
| JP | 2001-208850 A | 8/2001 | |
| JP | 200127247 A | 10/2001 | |
| JP | 2001-311777 A | 11/2001 | |
| JP | 2005-91314 A | 4/2005 | |
| JP | 2005-121583 A | 5/2005 | |
| JP | 2007-248408 A | 9/2007 | |
| JP | 2007-327967 A | 12/2007 | |
| JP | 2009-258119 A | 11/2009 | |
| WO | 95/30910 A1 | 11/1995 | |
| WO | 00/04403 A1 | 1/2000 | |
| WO | 2007/011214 A1 | 1/2007 | |
| WO | 2010/080046 A2 | 7/2010 | |
| WO | 2020/145999 A1 | 7/2020 | |

OTHER PUBLICATIONS

European Patent Office, International Preliminary Report on Patentability for application No. PCT/US2021/047030, dated Mar. 2, 2023, 16 pages.

European Patent Office (ISA/EP), International Search Report and Written Opinion issued in PCT application No. PCT/US2022/081897, dated Mar. 31, 2023, 40 pages.

European Patent Office, Communication Pursuant to Rule 164(2)(b) and Article 94(3) EPC for EP Patent Application No. 21773195.9, dated Apr. 15, 2026, 12 pages.

Soares, et al., "Development of a small gamma camera using wavelength-shifting fibres coupled to inorganic scintillation crystals for imaging 140keV gamma rays", IEE Transactions on Nuclear Science, vol. 46, No. 3, Jun. 1999, pp. 576-582.

\* cited by examiner

X-RAY TUBE 234

X-RAY CONE BEAM 342

2-DIMENSIONAL DETECTOR ARRAY 344

TARGET 114

X-RAY TUBE 234

BAG CONVEYOR 238

LINEAR DETECTOR ARRAY 240

TARGET 114

X-RAY FAN BEAM 236

TRANSMISSION DETECTOR 403

PMT 406

WIDE BEAM 512

114

SCAN DIRECTION OF BEAM 446

LOW RESOLUTION IMAGE 531

TRANSMISSION DETECTOR 403

PMT 406

NARROW BEAM 412

114

SCAN DIRECTION OF BEAM 446

HIGH RESOLUTION IMAGE 431

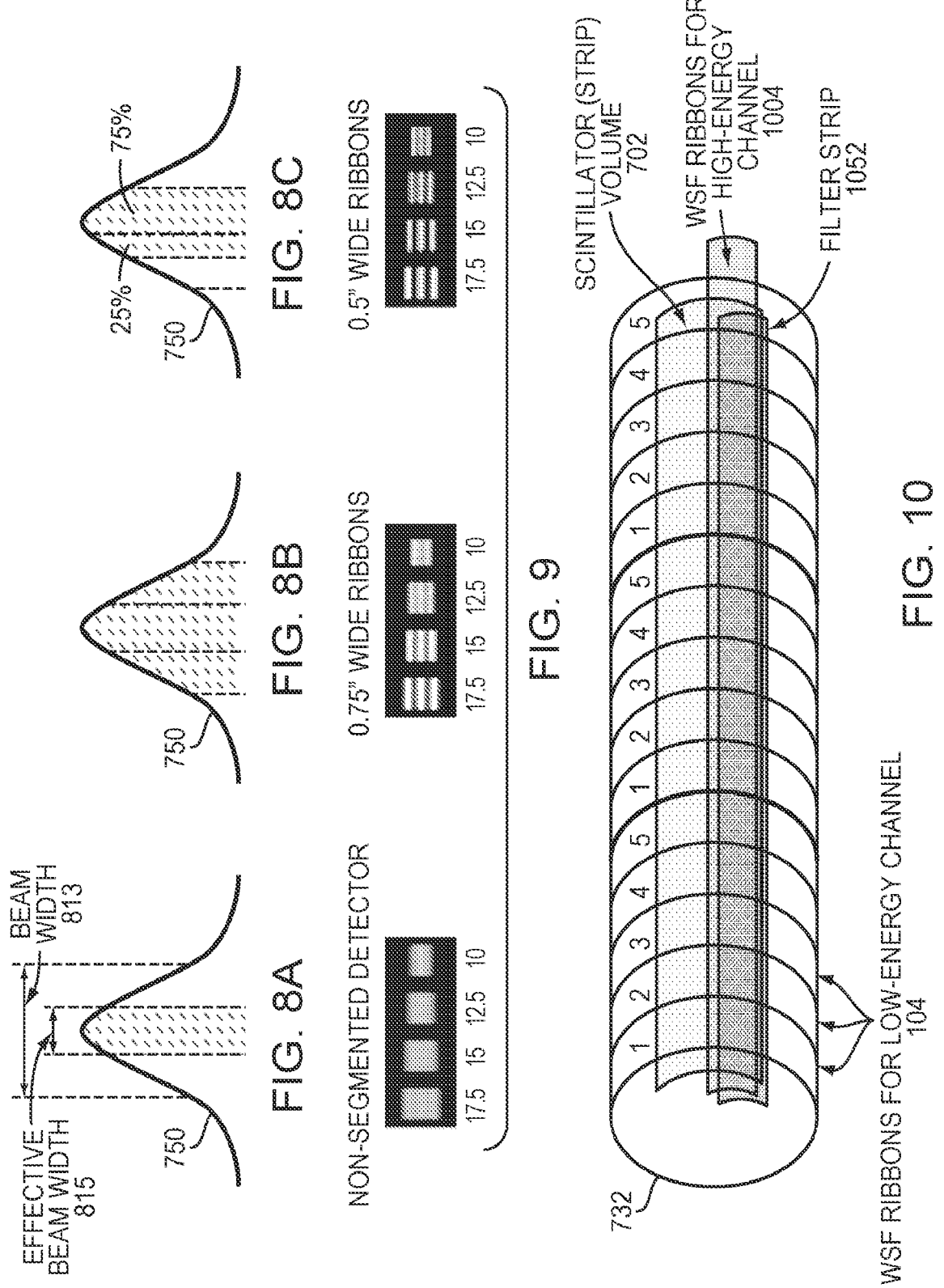

Note1: No detected x-ray from the incident beam passes through both the LE scintillator volume and the HE scintillator volume Note2: The HE filter, HE scintillator, and HE WSF ribbon all run the full length of the detector Note1: A single scintillator volume is used to detect both LE and HE x-rays Note2: The HE filter, shared scintillator, and HE WSF ribbon all run the full length of the detector

SCAN AXIS
110

770

110

1770

110

1870

SCAN AXIS
110

END
126

RIBBONS
104

EXAMPLE
LOCATIONS
OF SPATIAL
PERIODIC
ADJACENCY
124

CURVED OUTER
SURFACE
770

TUBULAR SUPPORT
STRUCTURE/SCINTILLATOR
VOLUME
1502

LIGHT DETECTION
STRUCTURE
1500

SUBSTANTIALLY
HELICAL
PATTERN
1572

END
126

1

X-RAY DETECTION STRUCTURE AND SYSTEM

RELATED APPLICATIONS

This application claims the benefit of U.S. Provisional Application No. 63/068,933, filed on Aug. 21, 2020, and U.S. Provisional Application No. 63/215,406, filed on Jun. 25, 2021. The entire teachings of the above applications are incorporated herein by reference.

BACKGROUND

The use of backscatter x-ray imaging for security applications is becoming more widespread for border security and for infrastructure protection. These systems require the use of scanning pencil beams of x-rays to form the scatter images and do not use fan beams of radiation as is typically used in transmission imaging systems. In addition to creating backscatter images, it is desirable to use the same scanning beam(s) of radiation to create transmission images. Unlike a fan beam, with which a segmented array of detector elements on the far side of the target object may be used to create a transmission image, a scanning pencil beam of x-ray radiation typically requires the use of a large monolithic scintillating medium on the far side of the target object to intercept the beam.

SUMMARY

As one example of a large monolithic scintillating medium, in drive-through backscatter x-ray portals, a long length of plastic scintillator has been used as a transmission detector to detect x-rays transmitted through the object in one of more of the x-ray views. Dual-energy versions of these large monolithic detectors have been used. Each of the previously known detector designs has advantages and disadvantages. For example, wavelength-shifting fiber (WSF) implementation on both low- and high-energy channels leads to a compact, low-profile design but tends to be an expensive approach, as the WSFs are expensive to manufacture. The use of plastic scintillator in the high-energy channel of the second design leads to a larger, less-compact and less-expensive detector.

WSF has been used as a convenient means to read out the scintillation light from various types of x-ray detectors, but not to enhance the performance of the detector otherwise.

Some embodiments disclosed in this application relate to the design of a relatively low-cost, compact, dual-energy transmission detector optimized for use with scanning pencil beams of x-rays, as used in backscatter imaging applications. Embodiments can have higher imaging resolution than systems that use equivalent x-ray scanning beam but which use prior art x-ray detector systems. Embodiments in their simplest form may include a single channel, single-energy detector that includes a scintillator screen coupled optically to multiple "ribbons" of wavelength shifting fibers (WSF) for collecting the scintillation light, where the fibers shift the scintillation light to a longer wavelength to allow for effective transmission along the fibers. As used herein, a "ribbon" is a set of one or more fibers—either a single fiber, or two or more fibers oriented in a configuration wherein the fibers are substantially parallel to each other. At least one end of each of the ribbons is optically coupled to a photodetector, such as a photomultiplier tube (PMT).

One embodiment includes a detector optimized for use with a scanning beam of x-rays. The detector includes:

a plurality of ribbons of wavelength-shifting fibers optically coupled to one or more scintillator volumes, wherein the ribbons are arranged to couple to the scintillator volume in a repeating pattern along one or more axes of the detector;

at least one photodetector coupled to one or more ends of each of the ribbons for detecting scintillation photons;

a signal combiner for combining the signals from one or more of the ribbons for each orientation of the scanning beam to create a combined signal for each beam orientation; and a processor for creating an image from the combined signals.

The signal combiner may be a lookup table or other means for combining the signals from one or more of the ribbons for each orientation of the scanning beam to create a combined signal for each beam orientation.

In one particular embodiment, a detector system for detecting a scanning beam of x-rays, the detector system includes one or more scintillator volumes configured to be oriented along a scan axis of a scanning beam of x-rays. The volume(s) are configured to receive x-rays from the scanning beam transmitted through a target, as well as to produce scintillation photons responsive to receiving the x-rays.

The system also includes a plurality of ribbons of wavelength-shifting fibers (WSFs) optically coupled to the one or more scintillator volumes along the scan axis via a spatial periodic adjacency of the plurality of ribbons to the scan axis. The ribbons are configured to receive scintillation photons from the scintillator volume(s) via the spatial periodic adjacency as the scanning beam of x-rays scans over the scan axis.

The system also includes at least one respective photodetector coupled to an end of each respective ribbon of the plurality of ribbons. Each respective photodetector is configured to detect the scintillation photons carried by the respective ribbon and to produce a respective signal responsively.

The system further includes a signal combiner configured to combine, selectively, respective signals from one or more ribbons of the plurality of ribbons, for positions of the scanning beam along the scan axis, to create a combined signal representing a scan of the target. The combined signal can represent the scan with enhanced spatial resolution.

In another embodiment, a light detection structure includes a tubular support structure having a curved outer surface. The light detection structure further includes a plurality of ribbons of wavelength-shifting fibers (WSFs) wrapped around the curved outer surface in a spatially periodic, substantially helical pattern. The plurality of ribbons of WSFs are configured to carry light to be detected at respective ends of respective ribbons of the plurality of ribbons.

In a further embodiment, an x-ray detection structure includes the light detection structure described above. The tubular support structure is comprised of one or more scintillator volumes configured to receive x-rays from an x-ray scanning beam. The scintillator volume(s) are optically coupled to the plurality of ribbons. The light to be detected includes scintillation photons produced by the one or more scintillator volumes responsive to receiving the x-rays from the x-ray scanning beam.

An alternative embodiment x-ray detection structure still includes the light detection structure described above. The scintillator volume(s) may be mechanically coupled to the tubular support structure, optically coupled to the plurality of ribbons of WSF, and configured to receive x-rays and to produce scintillation photons responsively. The WSF ribbons are configured to receive the scintillation photons and to convert the scintillation photons to the light to be detected.

In still a further embodiment, a detector system is configured to determine a characteristic of an energy spectrum of x-rays. The system includes a scintillator volume having an entrance surface and an exit surface. The entrance surface is configured to receive incident x-rays. The scintillator volume is configured to emit scintillation light responsive to the incident x-rays, and the exit surface is configured to pass a portion of the incident x-rays that traverse a thickness of the scintillator volume between the entrance surface and the exit surface.

The detector system further includes a first plurality of light guides optically coupled to the entrance surface of the scintillator volume. The system also includes a second plurality of light guides optically coupled to the exit surface of the scintillator volume.

In addition, the detector system includes at least one first photodetector optically coupled to an end of the first plurality of light guides and configured to output a first signal responsive to scintillation light from the scintillator volume. The detector system further includes at least one second photodetector optically coupled to an end of the second plurality of light guides and configured to output a second signal responsive to scintillation light from the scintillator volume.

In addition, the detector system includes a spectrum analyzer that is configured to receive the first and second signals responsive to the scintillation light from the scintillator volume and to determine a characteristic of an energy spectrum of the incident x-rays based on the first and second signals.

Variations of these embodiment and other embodiments will become apparent to those of ordinary skill in the relevant arts, including x-ray inspection, by reference to knowledge available to those of ordinary skill in the art and by reference to the full disclosure herein and the related drawings. Embodiment procedures for detection of scanning beams of x-rays may include using detectors according to any embodiments described herein.

BRIEF DESCRIPTION OF THE DRAWINGS

FIGS. 8A-8C are wide scanning beam profiles illustrating various beam segments that may be combined selectively by choosing signals from the WSF ribbons in FIG. 7 to achieve varying degrees of image resolution and/or penetration.

FIG. 9 illustrates results of a computer simulation showing images of a line pair phantom acquired with a standard prior-art detector (left), a detector with 0.75" wide ribbons (center), and a detector with 0.5" wide ribbons (right).

FIG. 10 is a perspective illustration of an embodiment dual-energy, high-resolution x-ray detector structure for use with a scanning x-ray beam as viewed from the direction of the incident beam.

Figure 1:
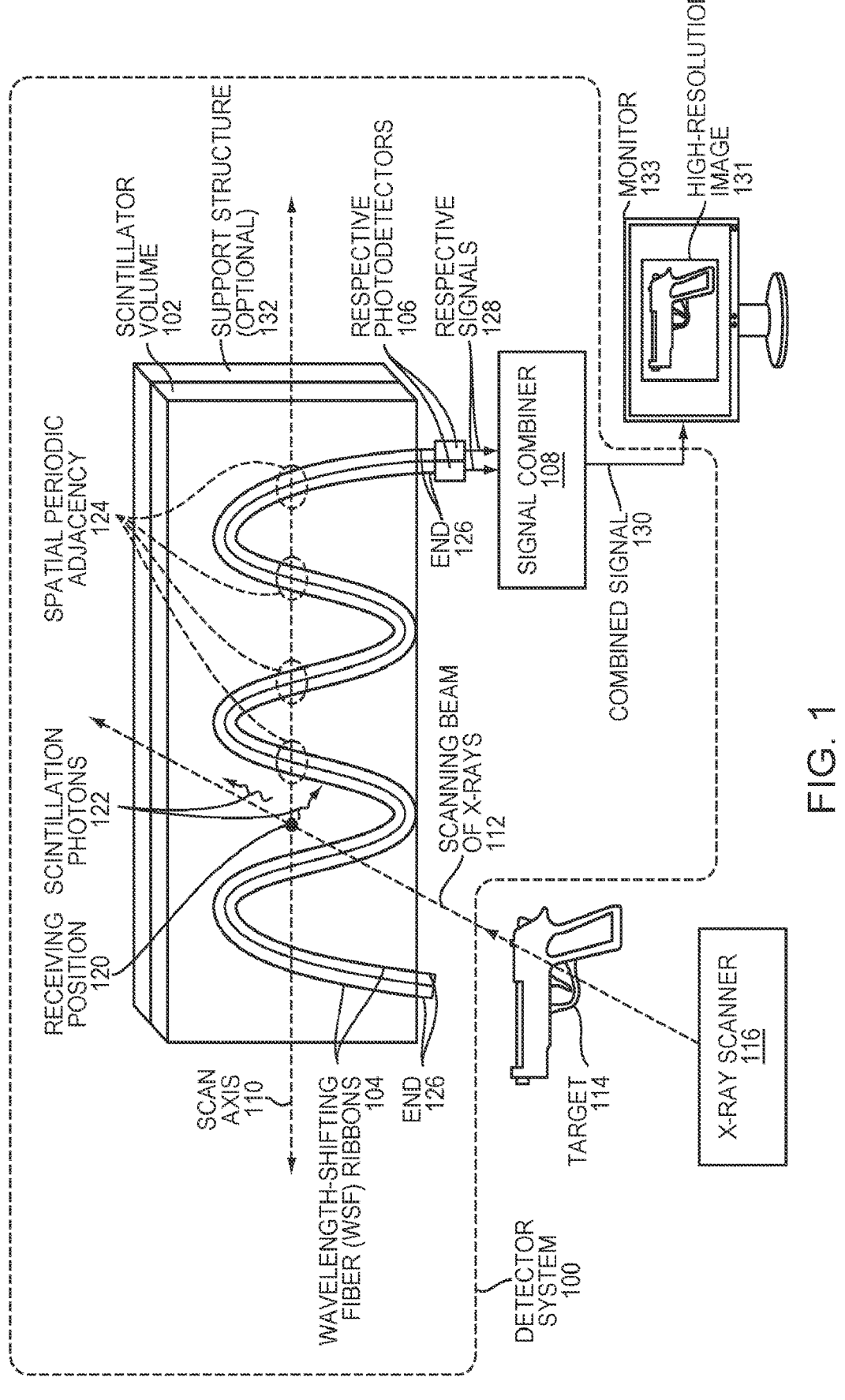
FIG. 1 is a schematic illustration of an embodiment detector system for detecting a scanning beam of x-rays.

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

FIG. 1 is a schematic illustration of an embodiment detector system for detecting a scanning beam of x-rays. The detector system 100 includes a scintillator volume 102, a plurality of wavelength shifting fiber (WSF) ribbons 104, respective photodetectors 106, and a signal combiner 108. The scintillator volume 102 is configured to be oriented along a scan axis 110 of a scanning beam of x-rays 112 that is transmitted through a target 114. The "scan axis" is also referred to herein as "scanning axis," "scanner axis," and the like. As one example, the scanning beam 112 may be received from an x-ray scanner 116, which can include a pencil beam scanning apparatus that is used for backscatter imaging and or transmission imaging, as is known in the art of x-ray scanning. The scintillator volume 102 is further configured to produce scintillation photons 122 responsive to receiving x-rays from the scanning beam of x-rays 112. The scintillator volume 102 illustrated in FIG. 1 can be replaced by more than one scintillator volume. In this case, scintillator volumes may be attached to each other contiguously or may have some separation between them.

A common feature of embodiments including aa single scintillator volume 102 or multiple scintillator volumes is that the WSF ribbons 104 are optically coupled to the one or more scintillator volumes along the scan axis 110 via a spatial periodic adjacency 124 of the ribbons 104 to the scan axis 110. As indicated above, the scanning beam of x-rays 112 is received at the scintillator volume 102 at various positions along the scanner axis 110. For example, a receiving position 120 is illustrated in FIG. 1. As the scanning beam interacts with the scintillator volume 102, the scintillation photons 122 are produced, and the scintillation photons (also referred to herein as "scintillation light," "light," and the like) will propagate in various directions through the scintillator volume 102. Some of the scintillation photons 122 will be optically coupled into fibers of the WSF ribbons 104. This optical coupling occurs predominantly and especially at receiving positions 120 where the ribbons 104 are adjacent to the scan axis. Example positions of spatial periodic adjacency 124 are illustrated in FIG. 1, where the optical coupling predominantly occurs. The plurality of ribbons 104 is configured to receive scintillation photons 122 from the one or more scintillator volumes via the spatial periodic adjacency 124 as the scanning beam of x-rays 112 scans over the scan axis.

In the embodiment of FIG. 1, the detector system 100 includes one respective photodetector 106 corresponding to each of the two WSF ribbons 104. However, in other embodiments, more than one respective photodetector 106 may be provided for each WSF ribbon 104. Each reason 104 may include a single WSF fiber or multiple WSF fibers. In the case of multiple WSF fiber ribbons start this sentence over. In the case of multiple WSF fibers in a given WSF ribbon 104, a photodetector may be configured to detect light carried by each WSF fiber of the respective WSF ribbon 104, for example. Nonetheless, multiple fibers in a WSF ribbon may have the light carried therein detected by the same respect respective photodetector 106.

The respective photodetectors 106 are coupled to respective and 126 of each respective ribbon of the plurality of ribbons 104. Each respective photodetector 106 is configured to detect scintillation photons 122 that are carried by the respective WSF ribbon 104. Each photodetector 106 responsively produces a respective signal 128, and these respective signals 128 are received by the signal combiner 108.

The signal combiner 108 is configured to combine, selectively, the respective signals 128 from one or more ribbons 104 of the plurality of rhythms. This combination that is selective occurs for positions of the scanning beam 112 along the scan axis 110. In this manner, a combined signal 130 is created by the signal combiner 108, and the combined signal 130 represents a scan of the target 114 with enhanced spatial resolution.

As described further hereinafter, the scanning beam 112 will have a particular beam width at the scanner axis 110, which is an axis along which the scanning beam 112 intersects with the scintillator volume 102. Prior art systems would typically be limited to a spatial resolution for an x-ray scan that is similar to the beam width of the scanning beam at the scanner axis 110. In other words, a positional uncertainty would be on the order of the size of the beam width at the scanner axis 110.

However, consistent with the detector system 100 and other embodiments described herein, a high-resolution scan may be obtained, with higher spatial resolution than would normally be obtained given the beam width. In other words, a positional uncertainty of the scanning beam 112 may be significantly smaller than the beam width of the scanning beam 112 at the scanner axis 110 through the scintillator volume. As illustrated in FIG. 1, the combined signal 130 may be used to create a high-resolution line scan, or multiple high-resolution line scans, such that a high-resolution image 131 of the target 114 can be created. In FIG. 1, the high-resolution image 131 is shown displayed on a monitor 133, for example.

In the schematic an illustration of FIG. 1, the spatial periodic adjacency 124 of the ribbons 104 to the scanner axis 110 in the scintillator volume 102 is achieved by way of the WSF ribbons 104 intersecting a path of the scanning beam of x-rays 112 in various periodic positions as the beam propagates toward the scanner axis 110 in the scintillator volume 102. The schematic FIG. 1 suggests the fiber ribbons 104 lie flat against the scintillator volume 102 at all positions. This need not necessarily be the case, however. In some embodiments, the WSF ribbons 104 can lie flat against the scintillator volume 102 only at the positions of spatial periodic adjacency 124, for example. The schematic FIG. 1 suggests that the spatial periodic adjacency 124 can be precisely periodic. However, while precise periodicity can be desirable, which precise spatial periodicity is not required in all embodiments.

Scintillation photons or scintillation light, as used herein, also referred to light that has been wavelength shifted in the WSF fibers and propagates therein to be detected by the respective photodetectors 106.

FIG. 1 also illustrates an optional support structure 132 the scintillator volume 102 and the WSF ribbons 104 can be mechanically coupled, such as being a fixed directly or indirectly, to the support structure 132. However, in other embodiments, the scintillator volume 102 forms a support structure to which the WSF ribbons 104 are mechanically coupled (e.g., affixed directly or indirectly). In particular, it is known that plastic scintillators can be formed into various convenient shapes and can also be formed with a sufficient, desirable rigidity to maintain spatial precision.

Schematic FIG. 1 illustrates the scintillator volume 102 as and the support structure 132 as being rectangular. However, in various embodiments, both the scintillator volume 102 and optional support structure 132 can take various forms that allow the scintillator volume 102 to be oriented along the scan axis 110, and also permit the WSF ribbons 104 to be oriented with respect to the scintillator volume 102 to achieve the spatial periodic adjacency 124. For example, in highly advantageous embodiments described hereafter, the optional support structure is tubular, and the scintillator volume 102 is a strip of scintillator material that is only wide enough to reliably encompass or capture the x-ray scanning beam 112 along the scan axis 110. Furthermore, the scintillator volume 102 itself can form a support structure and can be tubular in some embodiments.

The respective photodetectors 106 can be photomultiplier tubes (PMTs), for example.

The signal combiner 108 can be software operating on a computer system, such as a computer system that is used for controlling and displaying x-ray scanning, for example. In other embodiments, the signal combiner 108 can be a firmware routine operating in an embedded processing environment, for example.

A single scan along the scanner axis 110 can be a line scan, and a two-dimensional scan may be obtained by translating the target 114 or the x-ray scanner 116. In a case where the x-ray scanner 116 is translated, with respect to the target 114, the scintillator volume 102 and WSF ribbons 104 can be translated together with the scanner 116, for example.

Figures 15, 16, 17, 18:
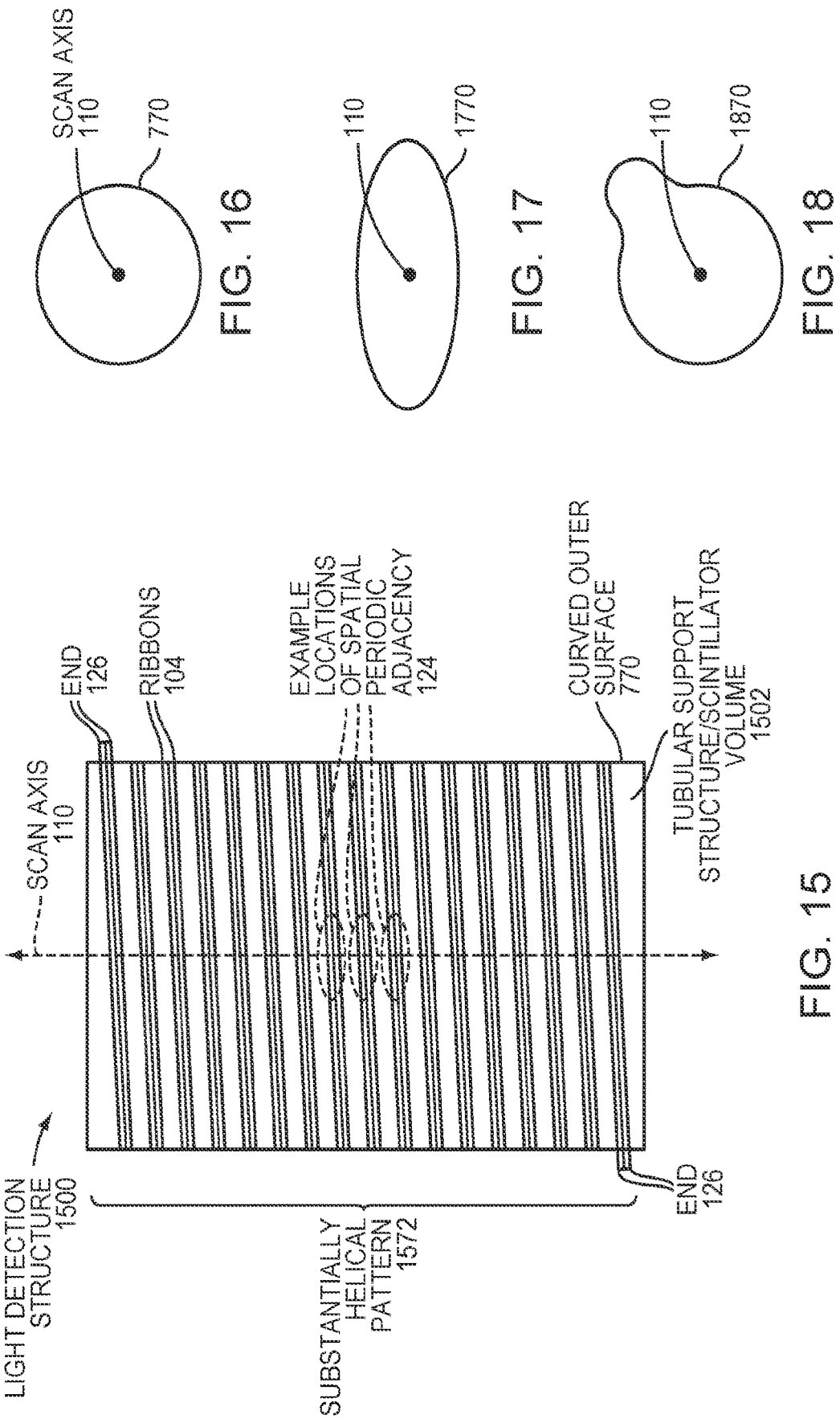
FIG. 15 is a profile-view illustration of an embodiment light-detection structure that has WSF ribbons wrapped around a curved outer surface of a tubular support structure.
FIG. 16 is a cross-sectional view of a tubular support structure having a circular cross section providing a curved outer surface.
FIG. 17 is a cross-sectional view of a tubular support structure having an oval cross section providing a curved outer surface.
FIG. 18 is a cross-sectional view of a tubular support structure having an irregular cross section providing a curved outer surface.

Characteristics of particular embodiments and variations of the detector system 100 will become apparent by reference to other drawings and the remainder of this description. In particular, the one or more scintillator volumes can itself or themselves form a support structure to which the plurality of ribbons are mechanically coupled, such as being directly affixed or indirectly coupled thereto, and FIG. 15 provides one example. As an alternative, the detector system may include a support structure as a component that is distinct from the scintillator volume(s) to which the volume(s) and the plurality of ribbons can be mechanically coupled directly or indirectly, and FIGS. 7, 14A, and 14B, among other drawings, are exemplary.

Figure 7:
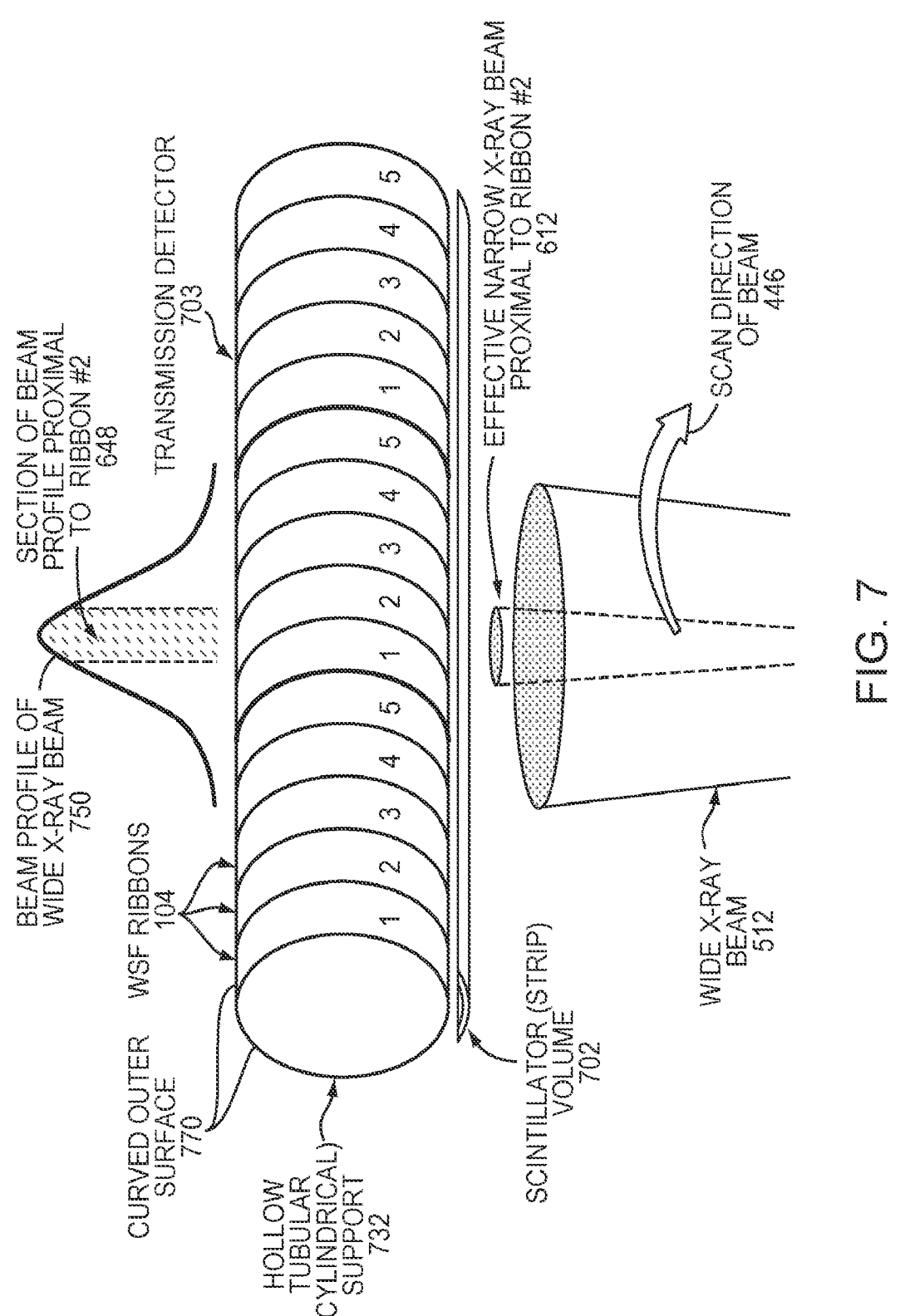
FIG. 7 is a perspective illustration of an embodiment x-ray detection system have a tubular support structure and spatially repeating series of WSF ribbons utilizing a wide scanning beam of x-rays with a detector readout system including a spatially repeating series of WSF ribbons that produces higher-resolution images.

The support structure can be a tubular support structure having a curved outer surface, such as the embodiments illustrated in FIGS. 7, 10, 12, 14A, 14B, and FIGS. 15-18. The plurality of ribbons mechanically coupled to the support structure can be wrapped around the curved outer surface of the tubular support structure in a substantially helical pattern to form the spatial periodic adjacency, as illustrated in FIGS. 7 and 15, for example, and especially in FIG. 15, which illustrates an example helical pattern with greater clarity. A tubular support structure may be solid or may have a hollow interior core.

The detector system may have a first ribbon and a second ribbon of the plurality of ribbons considered to be low-energy channel and high-energy channels, respectively, configured to receive scintillation photons produced by relatively lower-energy x-rays and relatively higher-energy x-rays, respectively, interacting with the one or more scintillator volumes. Scintillation photons carried by the high-energy channel can represent x-rays of higher average energy than scintillation photons carried by the low-energy channel. Example embodiment including this feature include FIGS. 10, 14A, and 14B.

Figure 14A:
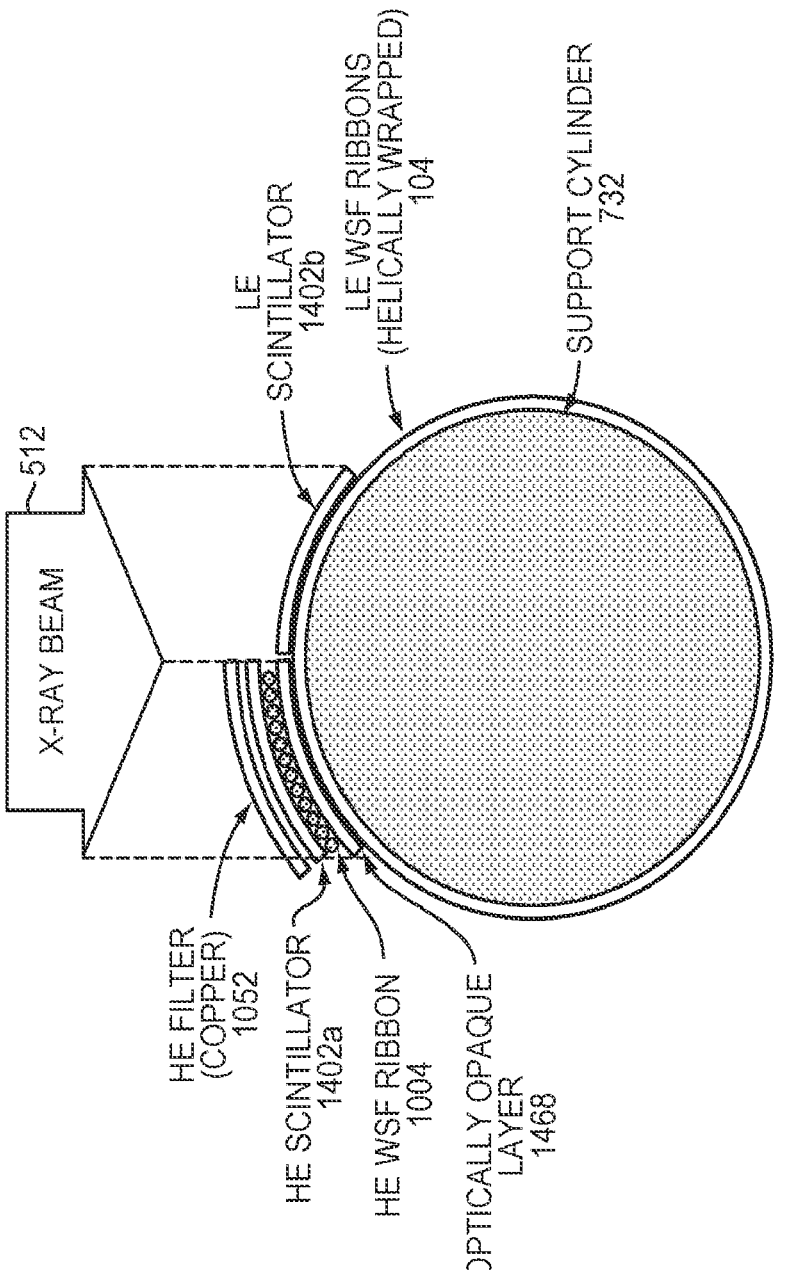
FIG. 14A is a cross-sectional illustration of an embodiment dual-energy detector with a tubular support structure and separate scintillator volumes for high-energy and low-energy channels, which correspond preferentially to high-energy and low-energy x-rays, respectively.
Figure 14B:
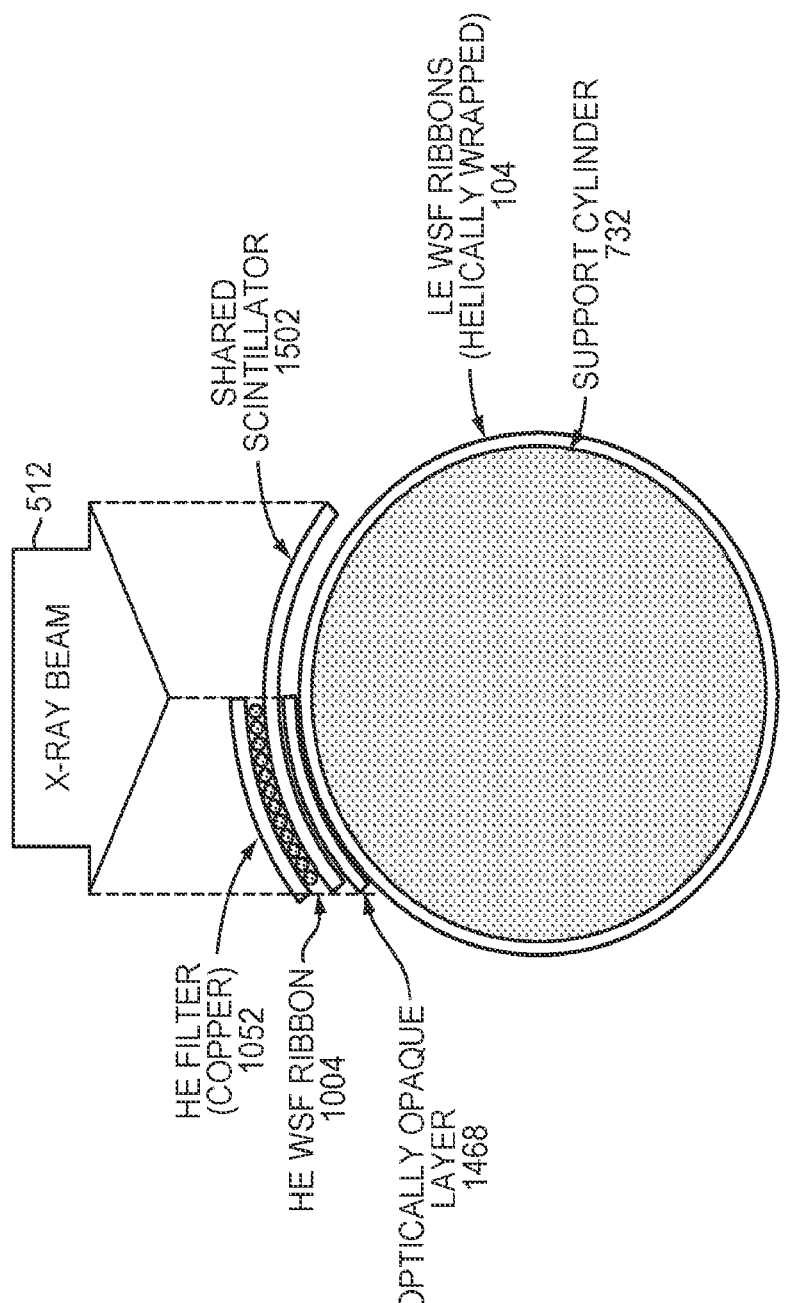
FIG. 14B is a cross-sectional illustration of an embodiment dual-energy detector with a tubular support structure and a common, shared scintillator volume for high-energy and low-energy x-ray channels.

The one or more scintillator volumes may include a single scintillator volume that produces scintillation photons carried by both the low- and high-energy channels. FIG. 14B is one exemplification of this feature. Alternatively, the one or more scintillator volumes may include first and second scintillator volumes that produce scintillation photons carried by the low- and high-energy channels, respectively. FIG. 14A is one exemplification of this feature.

Figures 22, 23:
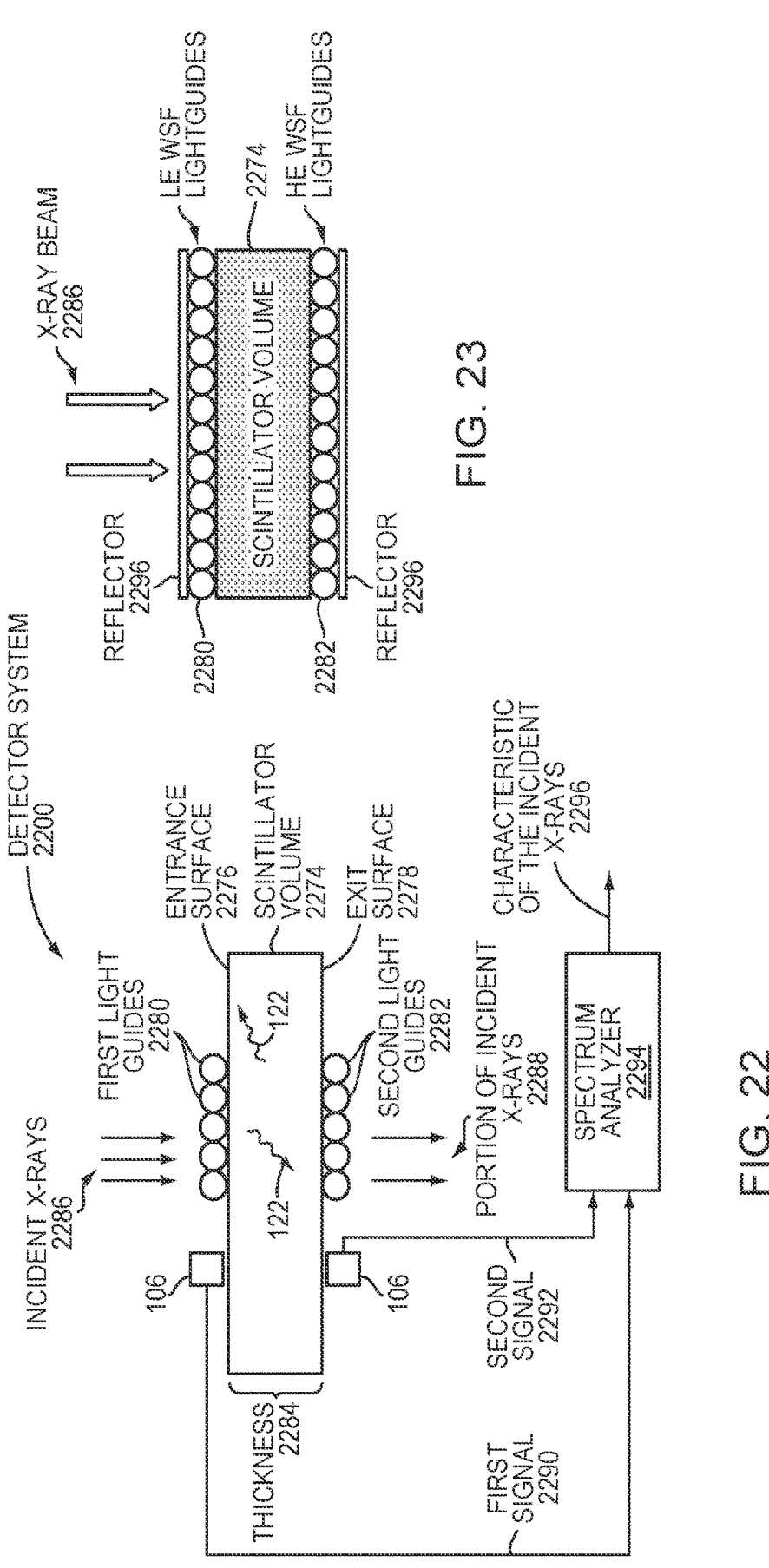
FIG. 22 is a schematic illustration of an embodiment detector system for determining a characteristic of an energy spectrum of x-rays.
FIG. 23 is cross-sectional view illustration of certain components of an embodiment detector system showing a scintillator volume used for both low-energy and high-energy channels in accordance with a preferred embodiment, with a central region of the detector, the scintillator volume, acting as a virtual filter (also referred to herein as an "effective self-filter") for enhancing energy discrimination.

The first scintillator volume can be thinner than the second scintillator volume, and FIG. 22 illustrates what is meant by scintillator thickness. The first and second scintillator volumes, such as those illustrated in FIG. 14A, can include respective scintillator materials optimized for detecting relatively lower-energy and relatively higher-energy x-rays, respectively. An x-ray filter may be situated between the low-energy and high-energy channels, with the x-ray filter configured to filter out lower-energy x-rays, as illustrated in example FIGS. 19 and 20. Where an x-ray filter is used, it may be material comprising one or more elements selected from a group consisting of Cu, Sn, Mo, and W.

Each ribbon in a plurality of WSF ribbons, such as the ribbons 104 illustrated in FIGS. 1 and 7, may include only one WSF. Alternatively, each ribbon can include more than one WSF, as illustrated by the multiple sub-ribbons (individual WSFs) 1204 included in each WSF ribbon 104 in the embodiment of FIG. 12, for example. The plurality of ribbons in the detector system can be sub-ribbons of a master ribbon of WSFs. As an example, in the FIG. 12 embodiment, the five WSF ribbons 104 helically wrapped around the hollow cylindrical support 732 can be considered as five WSF sub-ribbons, and the set of five WSF sub-ribbons can be manufactured to be connected and parallel with each other, for example, and they can form a single master ribbon that is helically wrapped around the support structure 732.

Figures 12, 13:
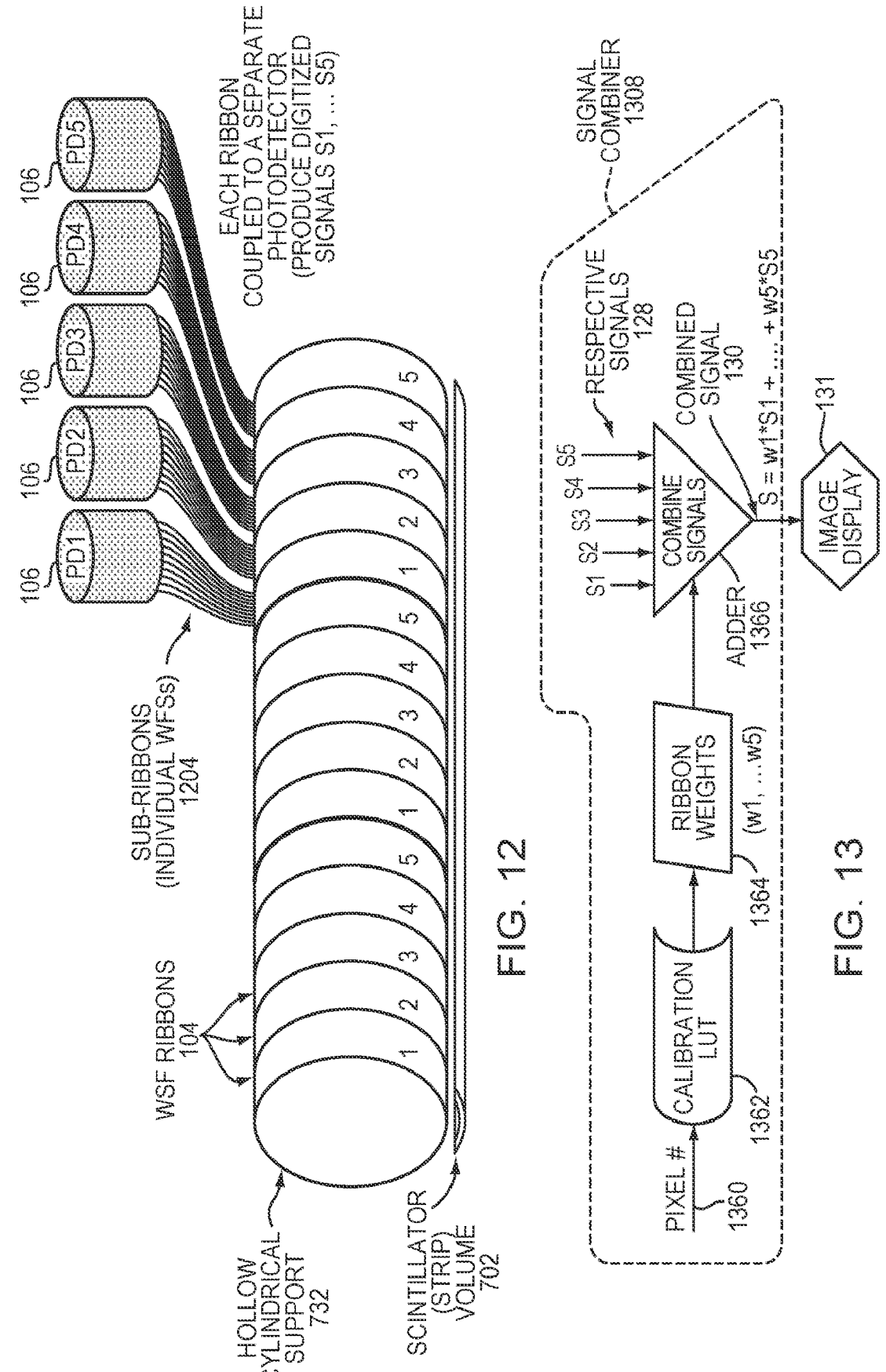
FIG. 12 is a schematic drawing illustrating respective photodetectors optically coupled to respective WSF ribbons that are wrapped around a tubular support structure according to an embodiment x-ray detector structure or system.
FIG. 13 is a block flow diagram illustrating functions of a signal combiner that may be used in embodiment x-ray detection systems.

The at least one respective photodetector coupled to an end of each respective ribbon, such as the photodetectors illustrated in example FIGS. 1 and 12, can be a photomultiplier tube (PMT). PMTs have the advantages of low dark current, as pointed out hereinabove. As illustrated in FIG. 12, each ribbon can include a plurality of sub-ribbons (individual WSFs). WSFs of each ribbon of a multi-fiber ribbon may be connected to only photodetector, or such WSFs may be optically coupled to respective photodetectors, such as respective anodes of a multi-anode PMT. For example, multi-anode PMTs are commonly available with 4-256 individual anodes, allowing 4-256 channels of input. The detector may be long enough to intercept the beam over an entire angle through which the beam is swept. Alternatively, the detector can be constructed out of shorter detector modules that are placed end-to-end to achieve full coverage of a swept beam. The at least one PMT described above may be an anode of a multi-anode PMT, and respective ribbons of the plurality of ribbons can optically coupled to respective anodes of the multi-anode PMT.

A scintillator material of the one or more scintillator volumes described above can include one or more materials selected from a group consisting of BaFCl, GOS, YOS, and ZnS.

Furthermore, in addition to embodiments specifically described herein, it will be apparent that other embodiments are included within the scope of the disclosure and claimed invention including various combinations of the elements of the specifically described embodiments. Moreover, it will become apparent that corresponding procedure for detection of a scanning beam of x-rays are also within the scope of embodiments, including using the detector system of any described embodiment or variation. It should be noted that an x-ray scanning beam with a substantially elliptical beam profile may be used to provide optimized imaging resolution in two orthogonal directions, and a detector system calibration may reflect such beam characteristic. Disclosed embodiment detector systems may also be adapted for use with an area detector suitable for scanning stationary objects.

Figure 3:
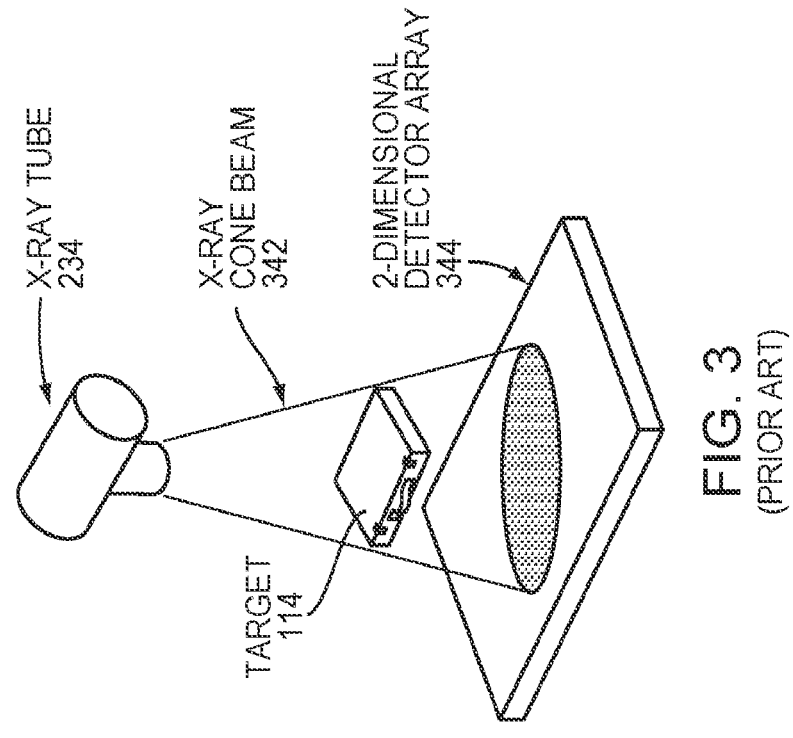
FIG. 3 (prior art) is a perspective illustration of an x-ray imaging system using a cone beam of x-rays incident on a two-dimensional segmented detector array.

Prior art x-ray transmission detectors that are used for imaging systems utilize a fan beam (FIG. 2) or a cone beam (FIG. 3).

Figure 2:
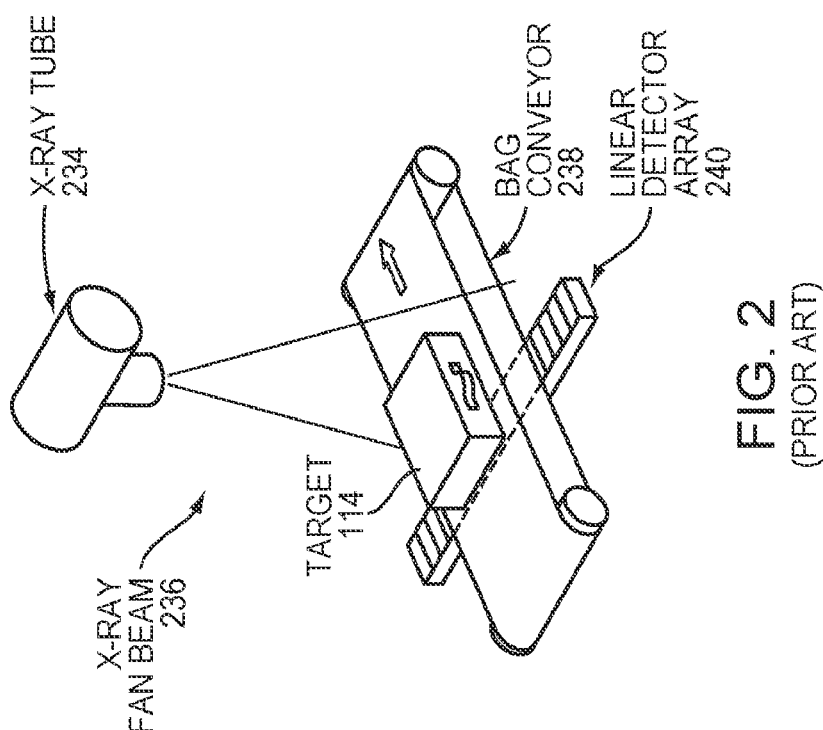
FIG. 2 (prior art) is a perspective illustration of an existing x-ray imaging system using a fan beam of x-rays incident on a linear segmented detector array.

FIG. 2 (prior art) particularly shows an x-ray tube 234 outputting an x-ray fan beam 236 to a target 114 that travels along a bag conveyor 238. A linear detector array 240 is positioned on the opposing side of the conveyor 238. In the case of the fan beam, the x-ray image is created by the detector measuring the intensity of x-rays transmitted through the object and striking each segment along the length of the detector 240. This is often referred to as a "linear segmented detector array." Typically, each segment or element of the linear array includes of a small piece of scintillator material that absorbs the x-rays and emits scintillation light, and the amount of light is then recorded by a solid state photodetector, such as a photodiode, optically coupled to the scintillator. The current from the photodiode corresponding to the light produced in each segment is digitized and corresponds to the intensity or brightness of one pixel in the image. The signal from all the detector elements in the linear array corresponds to one line of image pixels. By translating the object being imaged through the fan beam and acquiring a line of image data at many incremental positions during the translation, a full two-dimensional image of the object is acquired. Typically, several hundred lines of image data are acquired each second, with the acquisition of one line occurring in a few milliseconds.

FIG. 3 (prior art) is a perspective-view illustration of the x-ray tube 234 being used to create an x-ray cone beam 342 output toward a target 114. A two-dimensional detector array 344 is place on a side of the target 114 opposite the x-ray tube 234. In the case of imaging with a cone beam, the two-dimensional segmented detector array is used. For example, a flat panel detector used for very high-resolution imaging can include millions of square detector elements that are only 25 microns wide, yielding very high-resolution details in the image. In this case, only one acquisition is needed to acquire the full image, and no translation (of the object being imaged and/or the scanner) is required.

Because of the very large number of individual detector elements they contain, two-dimensional x-ray detectors (often referred to as "flat panel" detectors) such as the detector array 344 are very expensive. Because they contain photodiodes with a relatively high dark current, an integration time of a few milliseconds is typically required to produce an x-ray image with acceptable signal-to-noise characteristics. A shorter integration time produces images that are too noisy. Linear detector arrays (e.g., detector array 240 in FIG. 2) are less expensive but can still cost hundreds of dollars per inch of coverage, making large applications such as drive-through portals for vehicles very expensive. Since they typically also use photodiodes, they also require integration times of a few milliseconds.

In contrast to using a fan beam or cone beam of x-rays, backscatter imaging is achieved using a scanning pencil beam of x-rays. Unlike fan beam imaging, which creates an entire line of image data per acquisition period, backscatter imaging acquires one pixel at a time. Each point on the object being imaged is illuminated with the beam, and the intensity of the reflected x-rays is measured for each illumination point with large-area backscatter detectors. The intensity of the transmitted scanning beam can also be optionally measured, which is one subject of the current application. By raster-scanning the beam over the entire target object, a full two-dimensional image of the object can be obtained. Since an image line typically contains ~1000 pixels, the integration time per pixel must be about a thousand times shorter than the integration time for fan beam imaging. It must therefore be on the order of microseconds, instead of milliseconds in duration. This then rules out the use of solid-state photodetectors, such as photodiodes, because as described above, they typically require millisecond integration times due to their high dark current. The only photodetector currently available with low enough noise levels for backscatter imaging with a scanning beam is a photomultiplier tube (PMT), which has a dark current measured in nanoamps—about a thousand times lower than most solid-state photodetectors. However, these devices are quite expensive (hundreds of dollars per device versus a few dollars for premium photodiodes), yielding unacceptably high costs for an array with many hundreds of detector elements. They are also relatively large—the smallest PMT on the market is 12 mm in diameter, making it impractical to use them in large linear detector arrays.

Since only PMTs will suffice for backscatter imaging with a scanning x-ray beam, and it is impractical due to cost and size reasons to create segmented linear arrays with PMTs as the photodetectors, a monolithic non-segmented scintillator volume optically coupled to one or more PMTs must be used. The disadvantage of this approach is that because there is no positional information in the transmission detector, the imaging resolution of the system is completely defined by the width of the x-ray beam at the object being imaged. The transmission detector is measuring the transmitted intensity of x-rays through the object at each position of the beam during its scanning motion. It should be apparent that the clarity or resolution of the object being imaged depends on the width of the beam at the object.

Figures 4, 5:
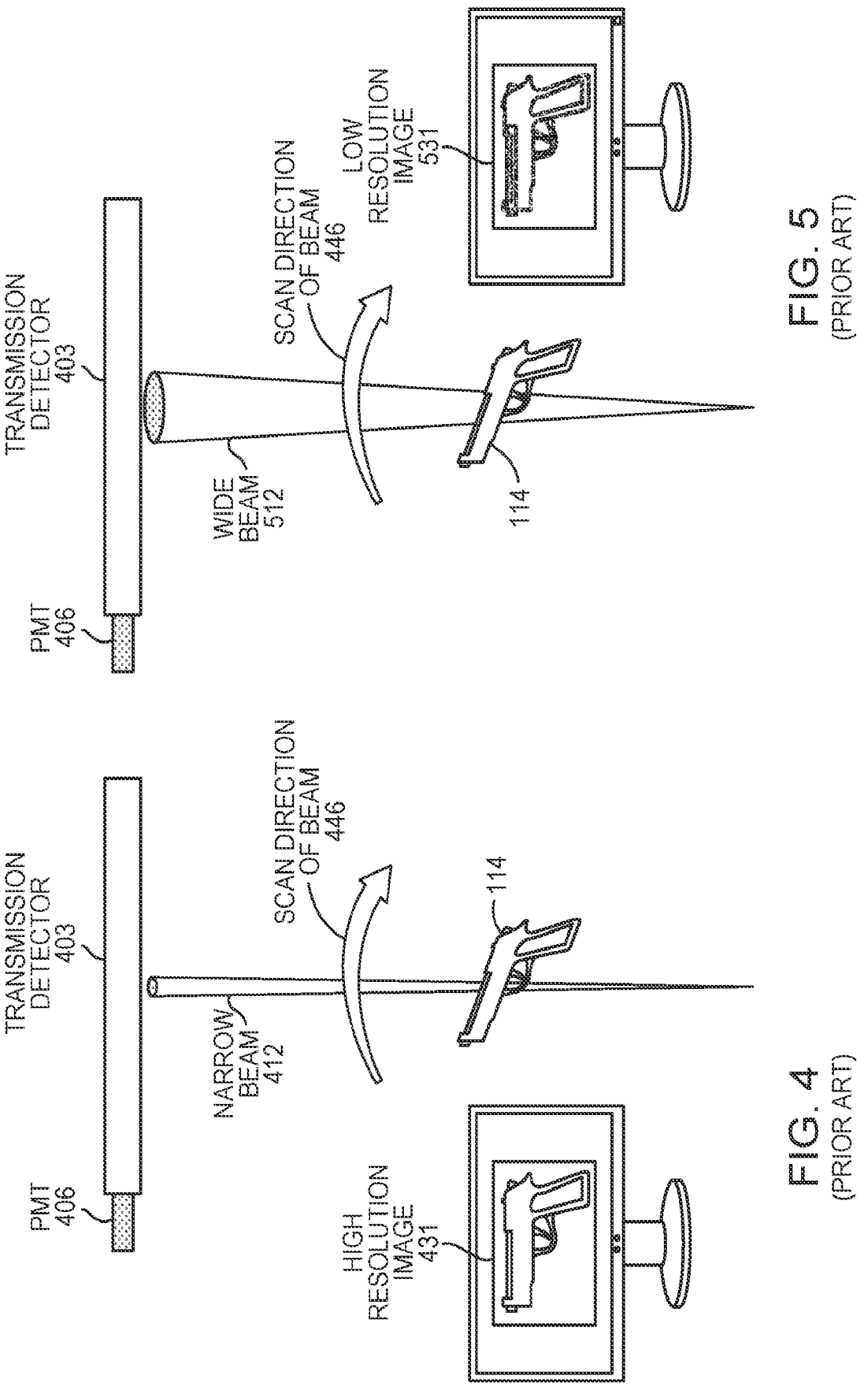
FIG. 4 (prior art) is an illustration of an existing x-ray imaging system utilizing a narrow scanning beam of x-rays.
FIG. 5 (prior art) is an illustration of an existing x-ray imaging system utilizing a wide scanning beam of x-rays.

FIG. 4 (prior art) is a schematic illustration of a transmission detector 403 with a PMT 406 optically coupled thereto, both used in connection with a narrow x-ray beam 412 used for backscatter imaging of a target 114. The narrow pencil scanning beam 412 sweeps over the target 114 in a scan direction 446, and signals from the PMT 406 are used to create a high-resolution transmission image 431, in addition to any backscatter images that are obtained.

With the narrow beam 412 of FIG. 4, the edges of the target object 114 in the transmission image 431 are sharp because the transition from unattenuated to fully attenuated will occur in just a few pixels.

FIG. 5 (prior art) illustrates a scanning setup similar to that of FIG. 4, except using a wide x-ray pencil scanning beam 512. It is possible to make the wide beam 512 to be wide deliberately in order to increase signal at the transmission detector. In other cases, a narrow x-ray pencil beam simply becomes broader as it continues to diverge over time and distance from the x-ray source. A low-resolution image 531 results in this case. With a broad/wide x-ray scanning beam 512, the transition from unattenuated to fully attenuated is gradual, and the edges of the object will appear to be blurred in the image over many pixels.

One solution to this problem is to make the beam narrower as in FIG. 4. This presents issues, however, because making the collimating aperture that defines the beam to be smaller reduces the number of x-rays in the beam, and the signal-to-noise ratio of the image at some point becomes unacceptable. In addition, there is a fundamental limitation on how small the beam can be made due to the beam penumbra, which is a consequence of the focal spot of the x-ray source having a finite width. The focal spot size is a function of the x-ray source power and cannot be made arbitrarily small. The higher the power of the source, the larger the focal spot must be to distribute the heat load over the anode and not melt the anode material. For a 2 kW source, the focal spot with a tungsten anode is typically 1-2 mm in diameter. This means that if a collimating aperture with a diameter of 1 mm is 10 cm away from the focal spot, the beam at 3.5 m from the focal spot will have a width of 7-10.5 cm (2.8-4.1 inches).

Embodiments consistent with the disclosure in this application use a novel means of reading out the scintillation light from a monolithic scintillator volume to provide transmission images of much higher resolution, even on a system that uses a wide scanning beam of x-rays as shown in FIG. 5. One aspect may be illustrated by comparison of the prior art system of FIG. 5 with a novel embodiment system shown in FIG. 6. In the FIG. 5 prior art transmission detector, the intensity of all the scintillation light produced in the scintillation material by the entire wide incident beam 512 is measured by the PMT 406. Since the signal from the entire beam 512 is being measured, the resolution of the resulting image 531 is poor because of the wide beam, as previously described.

Figure 6:
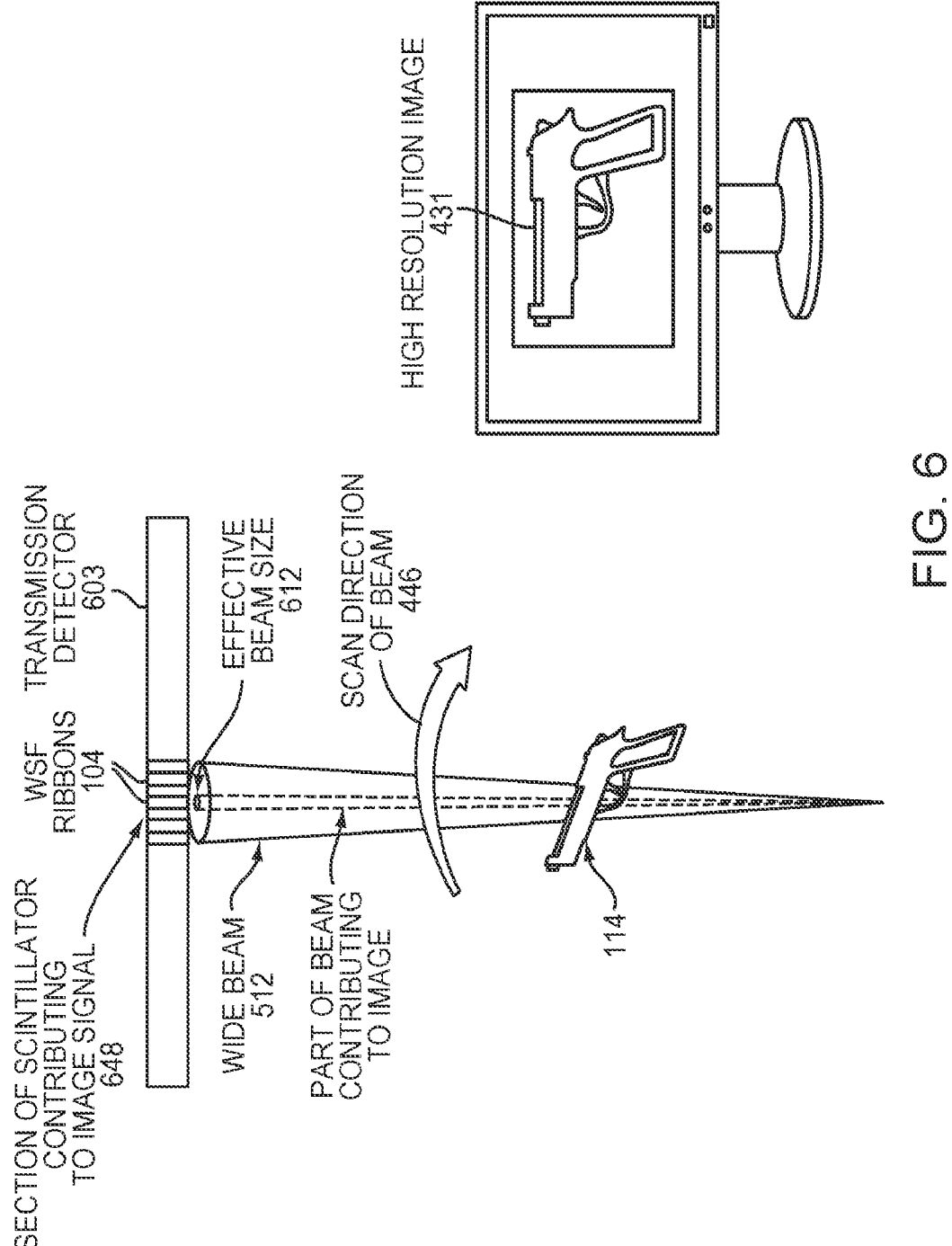
FIG. 6 illustrates a novel embodiment system similar to that of FIG. 5, except using detector segmentation that produces higher-resolution images even with a wide x-ray scanning beam.

FIG. 6 shows a novel setup for improving the image resolution, in which the scintillation light from each linear section 648 of the detector, of a series of linear sections 104, along the scan direction of the incident beam, can be separately measured. For example, if the scintillation light can be read out separately for each section 648 (e.g., 1 cm wide) of a scintillator transmission detector 603, then an effective beam width producing that signal will be only 1 cm wide at the detector, and substantially narrower at the location of the object being imaged. For the previous example of a transmission detector 3.5 m from the focal spot, an effective beam size 612 is reduced, resulting in an effective beam profile width being reduced from 7-10 cm down to approximately 1 cm, resulting in an example factor of 7-10 increase in imaging resolution along the scan direction 446 of the beam. In other embodiments, imaging resolution may be increased by an example factor of at least 1.5, at least 2, at least 5, at least 7, at least 10, 1.5-15, 2-10, 2-8, 2-7, 2-5, 5-7, or 5-10, when compared with measuring signal from an entire scanning beam as in FIG. 5. Note that for scanning beam systems, the resolution along the direction transverse to the beam scan plane is not an issue, because it is fixed either by the width of the active area of the transmission detector or by using collimating plates. In the current example, either of these can be adjusted to ensure that the effective beam width in the transverse direction is also 1 cm, resulting in an effective resolution in the image of 1 cm along both image axes. In this manner, the high-resolution 431. Example full beam width and example effective beam width are illustrated further in FIG. 8A and may be measured at half beam intensity profile height, as in the full width at half maximum (FWHM) method, for example. Width of a given linear section 648 in FIG. 6 can define effective beam width of the beam portion having the illustrated effective beam size 612.

Particular Single-Energy Embodiments

FIG. 7 is a schematic diagram of one single-energy embodiment x-ray detection structure 703 (also referred to herein as a "transmission detector") that may be used in an embodiment x-ray detection system. In this embodiment, the transmission detector or x-ray detection structure 703 includes a hollow tubular (specifically, cylindrical) support structure 732 of a material (for example plastic or aluminum), a set of "WSF ribbons" 104, and a scintillator (strip) volume 702. The combination of the support 732 and WSF ribbons 104 without the scintillator volume 702 should be understood to constitute a "light detection structure" as that term is used herein. The x-ray detection structure 703 may form part of an embodiment x-ray detection system.

The support structure 732 has a curved outer surface 770. Around the surface 770, the set of WSF ribbons 104 of wavelength shifting fibers (WSF) are wrapped in a helical pattern that is illustrated more particularly in FIG. 15. Each ribbon 104 can include a series of parallel wavelength shifting fibers, which may have a diameter of between 0.5 mm and 3 mm, for example. A typical effective diameter is 1 mm. The ribbons 104 may include anywhere from 5 to 50 parallel fibers, as an example, and may be physically attached to each other via an adhesive material, or the fibers may be embedded in an optically transparent matrix. Alternatively, the ribbons 104 may each include a single WSF or 2-4 WSFs, for example. The ribbons 104 are wrapped in such a way as to repeat their order along the length of the support 732 of the detector. For example, the embodiment shown has five ribbons labeled 1 through 5.

A strip of scintillating material 702, which is an example of the scintillator volume 102 described in connection with FIG. 1, is optically coupled along its entire length with the underlying WSF ribbons, is positioned on the side of the detector facing the incident beam. x-rays absorbed in the scintillator will produce scintillation light, which will preferentially enter the ribbon of fibers directly below it at spatial periodic adjacencies similar to those illustrated in FIG. 1. Only a small fraction of the scintillation light will be able to enter a neighboring ribbon not directly under the point of absorption of the x-ray in the scintillator due to the high self-absorption of the scintillation light in the scintillation material, so there is no easy path for this cross talk to occur. Thus, scintillation light is predominantly and preferentially optically coupled only into WSF fibers at the spatial periodic adjacencies. Once the scintillation light enters a wavelength shifting fiber, it is absorbed and re-emitted in the fiber at a longer wavelength. It can therefore not be reabsorbed in the fiber, and between 5% and 7% of the light that enters the fiber is trapped within the fiber and transmitted to one of the two fiber ends (not illustrated in FIG. 7, but similar to the fiber ends 126 in FIG. 1). At least one end of each of the ribbons 104 is connected to a separate PMT, or alternatively, to a separate anode of a multi-anode PMT, allowing the light output of each of the ribbons to be independently measured for each integration period as the beam scans across the length of the detector.

Still referring to FIG. 7, since the x-ray intensity absorbed in the scintillator proximal to each ribbon can now be separately measured for each ribbon, different parts of the beam can now be selectively used to read from more, or less, of the beam profile. "Combining signals," "signal combiner," and similar terms as used in this application refer to the configuration to combine one or more of the different parts of the beam, as selected from signals for respective ribbons, for combinations to achieve the best results for a given application.

FIGS. 8A-8C are x-ray beam intensity profiles 750 showing various (shaded) portions of signal from the wide x-ray beam 512 that may be used for different applications. For example, for the highest resolution imaging, just a central part/section 648 of the wide x-ray beam profile 750 corresponding to a central WSF ribbon can be selectively used to form the image (see FIG. 8A). Alternatively, the output signals from additional ribbons on each side of the central ribbon can also be used to form the image (see FIG. 8B). This would be desirable, for example, if the penetration through steel of the imaging system is critical, in which case higher beam intensity is more important than resolution. Since the beam will often be positioned such that its centroid is proximal to a point between two ribbons, a weighting can be implemented in a signal combiner, wherein the signal from more than one ribbon may be used, as shown in FIG. 8C. In this example, 25% of the signal from the left ribbon is combined with 75% of the signal from the right ribbon to produce a combined signal used to create the image. FIG. 8A also shows a beam width 813 of the wide x-ray beam 512 (FWHM) and an effective beam width 815 that is obtained by using only the signal corresponding to ribbon 2 in FIG. 7, corresponding to the effective narrow x-ray beam 612 illustrated in FIG. 7.

Detector Calibration

An initial calibration of an x-ray detector system, with no target objects in the beam, may be advantageously used to determine which ribbon signal (or combination of ribbon signals) should be used for each position of the scanning beam to achieve a scan objective. For example, if there are 1000 integration periods occurring during a single sweep of the beam across the detector (corresponding to 1000 pixels per image line), the software creating the image, such as a signal combiner according to various embodiments, may utilize a lookup table (LUT) such as that illustrated in FIG. 13 to assign a ribbon signal, or combination of signals, to form each pixel.

In the example of FIG. 8C given above in which two neighboring ribbon signals are combined in a weighted combination, for each pixel, the LUT would contain the two ribbon identifiers and the weighting to be applied to each. In other embodiments, a calibration process can include creating multiple LUTs. For example, one LUT can be used for the highest resolution mode for which signals from only one or two ribbons are combined, and another LUT can be used for the highest penetration, lowest resolution mode in which the signals from all the ribbons are used to create the image. Additional LUTs can be used for intermediate modes. It should be noted that an operator can be enabled to select the type of image that the operator would like to view in real-time and can be enabled to switch between the images at any time after the scan data has been acquired.

FIG. 9 shows simulated images from a computer simulation. A transmission image generated by a prior-art unsegmented transmission detector (FIG. 5) (left of FIG. 9) is compared with a detector using the setup shown in FIG. 8C with 0.75″ wide ribbons (center of FIG. 9) and 0.5″ wide ribbons (right of FIG. 9). The steady increase in image resolution can be seen from the left image to the right image. The phantom that was imaged in these simulations includes line-pair slots in a steel plate, with dimensions of 10 mm to 17.5 mm, as indicated in each of the left, middle, and right images of FIG. 9.

Note that the width and number of ribbons is preferably determined from the maximum width of the beam that is expected to be incident on the transmission detector. It is advantageous, but not essential, to have the number of ribbons, multiplied by the ribbon width, to be less than the maximum x-ray beam width to be measured. This will ensure that no ribbon is proximal to the beam at more than one location along the length of the detector.

Certain Dual-Energy Embodiments

Figures 19, 20, 21:
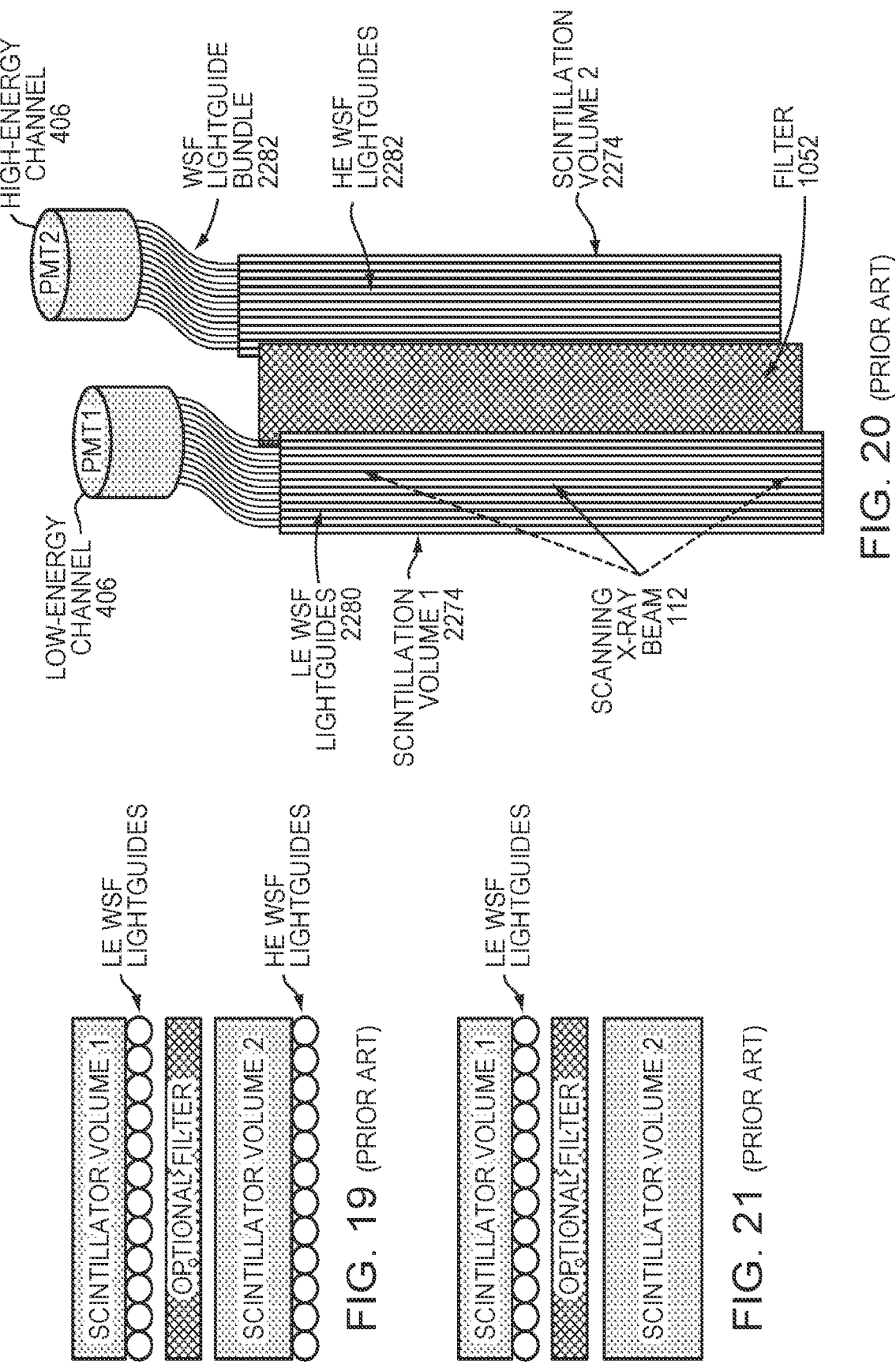
FIG. 19 (prior art) is a cross-sectional illustration of an existing dual-energy x-ray detector structure using two scintillator volumes, each read out by a plurality of WSF fibers.
FIG. 20 (prior art) is a perspective view of the same existing detector structure as in FIG. 19.
FIG. 21 (prior art) is a cross-sectional illustration of an alternative existing detector structure using two scintillator volumes, the first read out with a plurality of WSF fibers, and the second read out using other means.

The embodiments described so far have been single-energy detectors, in which there is no spectral discrimination of the incoming beam. Many transmission imaging applications can benefit from some form of material discrimination. This is typically done using "sandwich" style scintillation detectors, in which a first scintillator volume is sensitive to the low-energy component of the x-ray beam and a second scintillation volume, placed so that it intercepts x-rays that have penetrated the first scintillation volume, is sensitive to the higher-energy component of the x-ray beam. Prior art examples are illustrated in FIGS. 19-21. Many of these detectors additionally place a low-energy filter between the two scintillation volumes to enhance a separation in energy to which the two detector channels are sensitive. This filter often includes a thin sheet of 0.25-2.0 mm thick copper, but other filter materials are also often used.

A sandwich style dual-energy detector has previously been used, with either both scintillation volumes read out with WSF, or with only the first scintillation volume intercepted by the beam read out with WSF. The approach taken with the dual-energy embodiments in this application is to use WSF to read out both low-energy and high-energy channels with WSF, but to not use a sandwich-style detector. This means that a given x-ray cannot traverse both scintillation volumes, but the volumes can be presented to the incident beam side-by-side.

FIG. 10 is a perspective-view illustration of one embodiment of such a dual-energy configuration x-ray detection structure. A single scintillator volume 702 in strip form is used for both a low-energy detector channel (a plurality of WSF ribbons) 104 and a high-energy channel (a WSF ribbon) 1004. A filter strip 1052 of filtering material, such as copper or tin, covers one half of the scintillator strip along the length of the detector. The filter strip 1052 allows preferentially the higher-energy x-rays in the x-ray beam to reach the underlying scintillator volume strip 702. The scintillation light from the filtered side of the scintillator strip (corresponding to the high-energy "HE" channel side of the scintillator) is read out with the single ribbon 1004 of multiple WSFs that runs along the length of the detector structure, and is positioned between the scintillator and the other set of WSF ribbons 104 (low-energy channel) that are wrapped around the support structure 732.

Further referring to FIG. 10, scintillation light from the unfiltered side of the scintillation strip (corresponding to the low-energy "LE" channel) is read out with the previously described repeating set of WSF ribbons, which are wrapped around the detector as shown. An optically opaque material between the LE channel ribbons and the HE channel ribbon may be used to help ensure that there is no optical coupling (and hence no crosstalk) between the two channels.

It will be clear to those of ordinary skill in the art that the particular, previously described, dual-energy detector embodiment of FIG. 10 provides higher-resolution imaging only in the LE channel, and not in the HE channel. While this may appear to be a limitation of the design, most imaging systems that provide material discrimination require the use of an averaging kernel in the algorithm in order to get the required statistics when assigning a material characteristic to a given image pixel. This means that the material characteristic assignment used to colorize the image is already at a significantly lower resolution than the underlying image, so an intrinsic lower resolution of the HE channel data is not expected to be a significant limitation.

Other embodiments using this side-by-side dual-energy detector setup can use more than one WSF ribbon running the length of the detector to read out the scintillation light from the HE channel. This could, for example, be used to increase the resolution of the high-energy channel along the direction transverse to the length of the detector. Still other embodiments can use separate strips of the same scintillator material for both channels to reduce any potential crosstalk between the channels. Alternatively, a further embodiment can use two strips of differing scintillation materials, with one designed to enhance the detection of low energy x-rays, and the other chosen to enhance the detection of higher-energy x-rays.

Those skilled in the art will understand that such a detector is able to provide the operator with material discrimination. x-rays transmitted though high-Z materials such as steel have fewer low-energy x-rays remaining in the beam than x-rays passing through organic materials, such as water or plastic. By analyzing the relative ratio of detector signals in the low- and high-energy channels, material discrimination can be performed. This is typically indicated to the operator by applying a color pallet to the image: orange for organic materials with low effective atomic number (Z), green for intermediate-Z materials such as Al, and blue for higher-Z materials such as steel.

Additional embodiments of the system can use an elliptical or rectangular beam profile (rather than a circular or square profile) that is elongated in the direction along the detector width or along the detector length. In this way, resolution can be further optimized in either direction without decreasing the cross-sectional area of the beam (and therefore the intensity of x-rays in it).

Certain Embodiments for Scanning Stationary Objects

Handheld backscatter x-ray imaging instruments, such as the HBI-120 manufactured by Viken Detection Corp.™, can be used to scan, manually, stationary vehicles and objects such as abandoned parcels and bags. These instruments are typically used to create backscatter images of the object. However, by placing an unsegmented flat area detector behind the object, the intensity of the transmitted beam can also be measured, and a transmission image can be created. Unlike a scanning system in which the object is moved past or through the system, such as a baggage scanner with a conveyor or a drive-through portal for scanning vehicles, the handheld instrument typically images a stationary object. In this case, the instrument must be translated across the object during the scan. To acquire a transmission image with a line detector would require that the detector be translated simultaneously with the imaging system, which is usually not a practical possibility. Instead, a stationary area detector that is large enough to intercept the transmitted beam at all times during the scan is preferable, as shown in FIG. 11A.

Figure 11B:
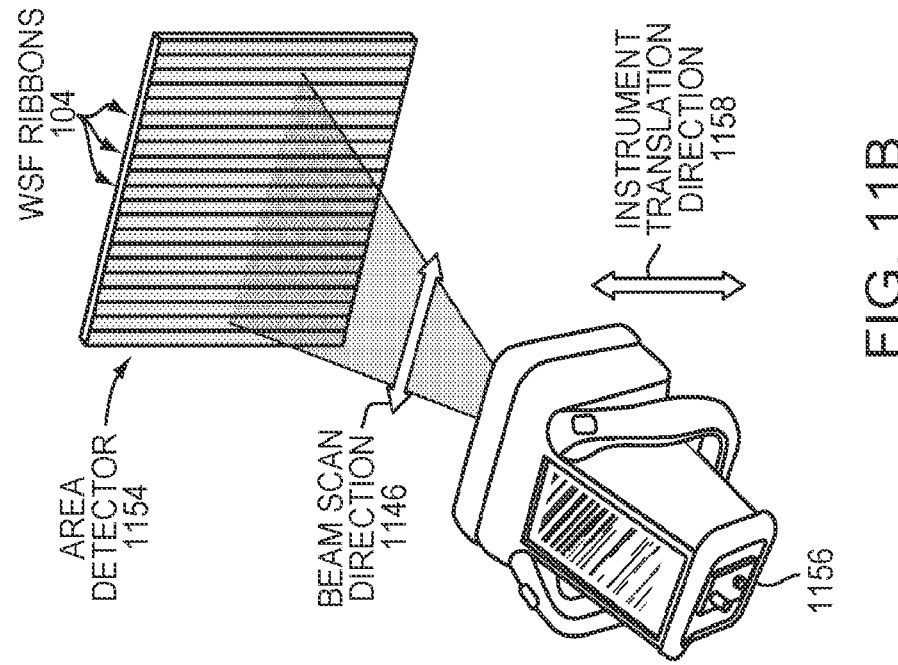
FIGS. 11A-11B illustrated embodiment detector structures adapted for use in an area panel detector.
Figure 11A:
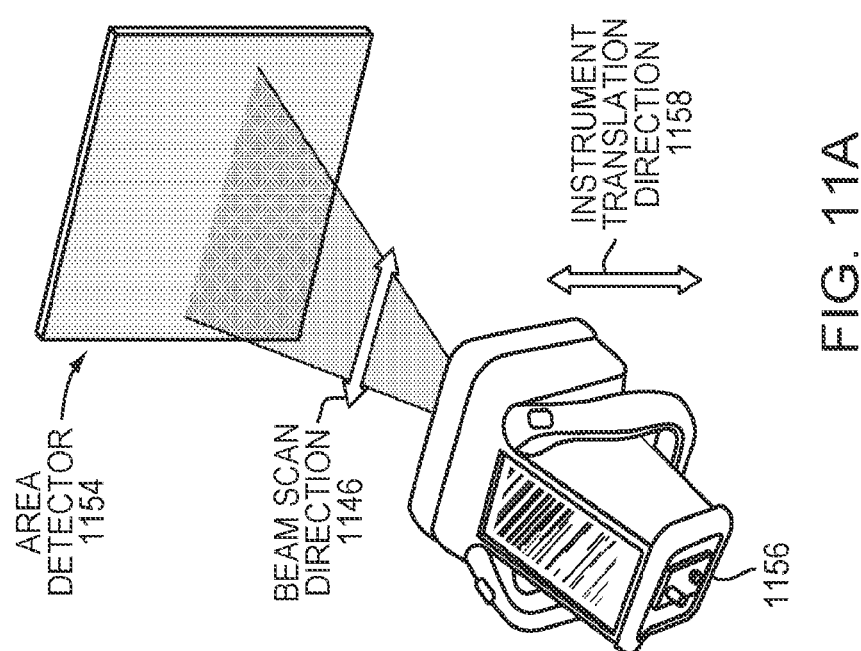

FIG. 11A is a perspective-view diagram illustrating a handheld backscatter imager instrument 1156 outputting an x-ray pencil beam having a beam scan direction 1146. In this example, the instrument 1156 is moved in a vertical translation direction 1158 to scan a target object (not shown) that is positioned in front of the area detector 1154.

FIG. 11B is a perspective-view diagram illustrating the handheld instrument 1156 being used with a further embodiment area x-ray detector structure 1155. In this embodiment, the WSF ribbons 104 are placed in a repeating pattern across a width of the detector structure 1155, allowing the resolution along the scan direction of the sweeping beam to be increased. The image resolution along the instrument translation direction is intrinsically higher due to the presence of internal collimators that are used to define a tighter beam profile along this direction.

Other Details of Embodiments

FIG. 12 is a schematic drawing illustrating respective photodetectors 106 optically coupled to respective WSF ribbons 104 that are wrapped around a hollow tubular (cylindrical) support structure 732 according to an embodiment. As illustrated in FIG. 12, each WSF ribbon 104 can be formed of multiple sub-ribbons (individual WSFs) 1204. In the embodiment of FIG. 12, all sub-ribbons 1204 in a given ribbon 104 are optically coupled to the same photodetector 106. However, in other embodiments, individual WSFs 1204 of a given multi-WSF ribbon 104 may be detected by a separate photodetector.

FIG. 13 is a block flow diagram illustrating an example signal combiner 1308 that may be used in embodiment x-ray detector systems. FIG. 13, as an example, assumes a set of five WSF ribbons 104, with five respective photodetector signals s1-s5 output from respective photodetectors 106, as in the embodiment of FIG. 12. At 1360, pixel numbers are designated to a calibration lookup table (LUT). Detector pixels consistent with various embodiments are described above. At 1362, the LUT outputs ribbon weights w1-w5 corresponding to given pixel numbers. At 1364, the ribbon weights are input to an adder 1366, which also accepts respective signals 128 (s1-s5) from the photodetectors 106 and combines the signals. The adder 1366 calculates and outputs a combined signal S 130 according to $S=w1*s1\_ . . . +w5*s5$. The combined signal S 130 can be in a form representing a line scan, or multiple line scans, such that the combined signal S 130 can represent part or all of an image 131 that can be displayed to a user.

All or part of the signal combiner 1308 may run within a computer processor, embedded processor, or other processor. In a particular example, the LUT forms part of, and is stored in, computer memory or a type of non-volatile memory such as an EEPROM. The adder 1366 may include computer code that is executed in a computer processor, an embedded processor, or the like. In the example of FIG. 13, the signal combiner 1308 includes both the predefined LUT function and signal combination/adder function. However, in another embodiment, the signal combiner includes only the adder 1366, and either the LUT function is considered to be part of another component, or the combiner 1308 uses another means of combining the one or more signals.

Embodiment detector systems may further include a processor configured to create an image from the combined signal.

Other Dual-Energy Embodiments

FIG. 14A is a cross-sectional diagram of an embodiment x-ray detection structure that takes advantage of helically wrapped WSF ribbons and provides dual-energy x-ray detection and discrimination, for detecting a scanning x-ray beam with enhanced spatial resolution, even when the scanning x-ray beam is relatively large. The x-ray detection structure of FIG. 14A includes the cylindrical support structure 732 illustrated in other embodiments. Around the cylindrical support structure 732 are wrapped a plurality of wavelength shifting fiber WSF ribbons 104 that are wrapped in helical fashion as previously described, and as described in further detail hereinafter in connection with FIG. 15. The plurality of WSF ribbons 104 constitute a low energy (LE) channel configured to detect, preferentially, lower energy x-rays. An LE scintillator volume 1402*b* covers a portion of the ribbons 104 and is configured to receive the x-rays from a portion, such as approximately half, of the wide x-ray beam scanning beam 512.

A high-energy (HE) filter 1052, in this case made of copper, is configured to receive x-rays from the other half of the x-ray beam 512, thus blocking preferentially lower energy x-rays from reaching a high-energy HD scintillator volume 1402*a*. A high-energy (HE) WSF ribbon 1004 is situated underneath the HE scintillator 1402*a* and is configured to interact with the higher energy x-rays to produce scintillation light. Via an optical coupling between the HE WSF ribbon 1004 and the HE scintillator 1402*a*, scintillation photons corresponding to the higher energy x-rays are optically coupled into the HE WSF ribbon 1004. An optically opaque layer 1468 situated between the HE WSF ribbon 1004 and the support cylinder 732 further assist in blocking scintillation photons resulting from higher energy x-rays from being coupled into the helically wrapped LE WSF ribbons 104.

In the manner illustrated in FIG. 14A, no detected x-rays from the incident beam 512 pass through both the LE scintillator volume 1402*b* and the HE scintillator volume 1402*a*. Furthermore, although not visible in the cross-sectional view of FIG. 14A, the HE filter 1052, HE scintillator 1402*a*, and HE WSF ribbon 1004 all extend a full length of the detector structure, similar to various components described in connection with FIG. 10.

FIG. 14B is a cross-sectional view diagram of an alternative dual-energy x-ray detection structure that may form part of various embodiments x-ray detection systems. The embodiment of FIG. 14B is similar in many respects to the embodiment of FIG. 14A, except that a shared scintillator volume 1502 is used for both high-energy and low-energy channels. Thus, the shared scintillator 1502 receives substantially all of the scanning x-ray beam 512, covering both low-energy and high-energy portions of the detector structure. On the low-energy (right) side, all x-rays, low-energy and high-energy, are allowed to interact with the shared scintillator volume 1502. Thus, scintillation photons produced by the low-energy side of the scintillator volume 1502 that result from both high-energy and low-energy x-rays may be optically coupled into the LE WSF ribbons 104.

On the other hand, on the left (HE) side of the x-ray detection structure, the HE filter 1052 passes preferentially higher energy x-rays from the left half of the x-ray beam 512. In this manner, scintillation photons produced by the left side of the shared scintillator 1502, which are optically coupled into the HE WSF ribbon 1004, predominantly result from higher energy x-rays. The x-ray detection structure of FIG. 14B also includes the optically opaque layer 1468, which assists in preventing scintillation photons produced on the left side of the shared scintillator 1502 from reaching the LE WSF ribbons 104. Although not visible from the cross-sectional view of FIG. 14B, the HE filter 1052, shared/common scintillator 1502, and HE WSF ribbon 1004 all extend a full length of the detector structure.

Certain Embodiment Light Detection Structures and X-Ray Detection Structures

FIG. 15 is a side view illustration of a light detection structure 1500 according to an embodiment. The light detection structure 1500 includes a tubular support structure 1502 having a curved outer surface 770. The structure 1500 also includes a plurality of ribbons 104 of WSFs wrapped around the curved outer surface 770 in a spatially periodic, substantially helical pattern 1572. The plurality of ribbons of WSFs are configured to carry light to be detected at respective ends 126 of the plurality of ribbons 104. In some embodiments, detection occurs only at one end 126 of each of the plurality of ribbons 104. However, in other embodiments, light detection occurs at both ends of each WSF ribbon 104.

As will be understood by reference to other parts of this description, the light detection structure 1500 may form part of an x-ray detector and detection structure that includes a scintillator volume that interacts with x-rays to produce scintillation light that is optically coupled into the plurality of WSF ribbons 104. In turn, the x-ray detection structure may form part of an x-ray detection system as described in connection with FIG. 1 and other figures.

The tubular support structure 1502 in the particular light detection structure 1500 of FIG. 15 is formed of a scintillator material and forms a scintillator volume. In other embodiments, the single scintillator volume 1502 may be replaced by scintillator volume sections (i.e., multiple scintillator volumes that are configured to receive x-rays from an x-ray scanning beam. The scintillator volume 1502 is optically coupled to the plurality of ribbons 104, at least at locations of spatial periodic adjacency 124 of the ribbons 104 to a scanner axis 110 of a scan beam. Responsive to receiving x-rays from the x-ray scanning beam (not shown in FIG. 15), scintillation photons are produced by the scintillator volume 1502 and detected at at least one end 126 of each of the ribbons 104. In this manner, the light detection structure 1500, because it includes the scintillator volume/tubular support structure 1502, may also be considered and referred to herein as an x-ray detection structure.

It should be noted that scintillation photons comprising the light to be detected may be wavelength-shifted in the plurality of ribbons of WSFs. Both scintillation photons directly produced by the scintillator volume 1502, and wavelength-shifted scintillation light, are referred to herein as "scintillation photons," "scintillation light," "light to be detected," and the like.

In other embodiments, the tubular support structure 1502 is not a scintillator volume, such that the light detection structure 1500 is not considered to be an x-ray detection structure. However, in certain embodiments, one or more scintillator volumes may be mechanically coupled to the tubular support structure 1502 and optically coupled to the plurality of WSF ribbons 104. The one or more scintillator volumes can be configured to receive x-rays and to produce scintillation photons responsively. The plurality of ribbons of WSF are configured to receive the scintillation photons and to convert the scintillation photons to the light to be detected. Thus, a separate scintillator volume is provided, separate from the support structure, as in various other figures.

In some embodiments, the separate scintillator volume may take the form of the strip scintillator volume 702 of FIG. 10, the LE scintillator 1402*b* or HE scintillator 1402*a* of FIG. 14A, or the shared scintillator 1502 of FIG. 14B, for example. Where a separate scintillator volume is provided as described, the light detection structure 1500, together with the scintillation volume, form an x-ray detection structure, which in turn, may form part of an x-ray detection system described in connection with FIG. 1 or other figures.

Additional Dual-Energy Embodiments

Many transmission imaging applications have a requirement that there be some form of material discrimination. This is typically done using "sandwich"-style scintillation detectors, in which a first scintillator volume is sensitive to the low-energy component of the x-ray beam and a second scintillation volume, placed so that it intercepts x-rays that have penetrated the first scintillation volume, is sensitive to the higher-energy component of the x-ray beam. Many of these detectors additionally place a low-energy filter between the two scintillation volumes to enhance the separation in energy to which the two detector channels are sensitive. This filter often consists of a thin sheet of 0.25-2.0 mm thick copper, but other filter materials are often used.

FIG. 19 (prior art) and FIG. 20 (prior art) illustrate existing dual-energy x-ray detector structures. Existing systems use a sandwich-style dual-energy detector with two separate scintillation volumes, with either both scintillation volumes read out with WSF, as in FIG. 19 (prior art) and FIG. 20 (prior art), or with only the first scintillation volume intercepted by the beam read out with WSF and the second scintillation volume read out by some other means, as in FIG. 21 (prior art).

FIG. 20 (prior art) particularly shows a scanning x-ray beam 112 received at a sandwich-style detector including a scintillation volume 1 2274 having LE WSF light guides 2280 coupled thereto. The LE WSF light guides 2280 are read out by an LE channel PMT 1 406. Higher-energy x-rays that penetrate a filter 1052 situated between LE and HE channels are received by a scintillation volume 2 2274, which is optically couple to HE WSF light guides (WSF light guide bundle) 2282. The HE WSF light guides 2282 are read out by an HE channel PMT 2 406.

The approach taken with the embodiments in this application is to not use a sandwich-style detector containing two scintillation volumes, but to take advantage of one relatively thick scintillation volume for both low-energy and high-energy channels, and to read out each channel with WSF optically coupled to opposite sides of the relatively thick scintillator volume.

FIG. 22 is a schematic diagram illustrating an embodiment detector system 2204 determining a characteristic of an energy spectrum of x-rays. The detector system 2200 includes a scintillator volume 2274 having an entrance surface 2276 and an exit surface 2278. The entrance surface 2276 is configured to receive incident x-rays 2286. The incident x-rays 2286 may be from a scanning x-ray beam, also referred to herein as a sweeping x-ray beam, a stationary x-ray beam, such as a cone beam, or a fan beam, for example.

The scintillator volume 2274 is configured to emit scintillation light 122 responsive to receiving the incident x-rays 2286. The exit surface 2278 is configured to pass a portion of the incident x-rays 2286 that traverse a thickness 2284 of the scintillator volume 2274 between the entrance surface 2276 and the exit surface 2278.

The detector system 2200 further includes a first plurality of light guides 2280 that are optically coupled to the entrance surface 2276 of the scintillator volume 2274. The system 2200 also includes a second plurality of light guides 2282 that are optically coupled to the exit surface 2278 of the scintillator volume 2274.

The system includes at least one first photodetector 106 that is optically coupled to an end of the first light guides 2280. The first photodetector is configured to output a first signal 2290 responsive to the scintillation light 122 from the scintillator volume 2274. The system also includes at least one second photodetector 106 that is optically coupled to an end of the second plurality of light guides 2282 and is configured to output a second signal 2292 responsive to the scintillation light 122 from the scintillator volume 2274. Although ends of the first and second light guides are not specifically illustrated in FIG. 22, it should be understood what is meant by ends of the light guides by reference to FIG. 1, FIG. 15, and other drawings and corresponding descriptions herein.

The detector system 2200 further includes a spectrum analyzer 2294 that is configured to receive the first and second signals 2290, 2292 responsive to the scintillation light and to determine a characteristic of an energy spectrum a characteristic 2296 of an energy spectrum of the incident x-rays 2286 based on the first and second signals 2290, 2292.

The characteristic 2296 can include, for example, relative signal strength for at least two different wavelength segments of an energy spectrum of the incident x-rays 2286, for example. The characteristic 2296 alternatively can include an indication of a material or a material class of a target object through which the incident x-rays 2286 pass, or from which the incident x-rays 2286 are scattered. Identification of a material or material class of the target, or of other characteristics 2296 of incident x-rays incident on a dual energy x-ray detector, are known to those of skill in the art and are within the scope of this disclosure. However, such characteristics have not been previously determined with the benefit of a detector system such as the detector system 2200, which takes advantage of a single, common scintillator volume 2274 and relies on self-attenuation of scintillation light within the scintillator volume 2274 in order to achieve energy discrimination in the manner illustrated and described.

The spectrum analyzer may be a computer processor or an embedded processor or the like. It may output the characteristic of the energy spectrum, directly or indirectly, to a communication interface, a display, a printout, a human, etc.

The thickness of the scintillator volume can be larger than a self-attenuation length of a scintillator material of the scintillator volume. The scintillator volume can be a strip scintillator volume configured to receive the incident x-rays at the entrance surface thereof, from a sweeping x-ray beam transmitted through a target, over a sweep of the sweeping x-ray beam, such as the strip scintillator volume 702 of FIG. 7. The scintillator volume can be an area scintillator volume similar to the area detectors of FIGS. 11A-11B, for example. The scintillator volume may be configured to receive the incident x-rays at the entrance surface via x-ray scattering from a target. However, incident x-rays may alternatively be received at the entrance surface via passive emission from a target.

The first and second pluralities of light guides can be wavelength-shifting fibers (WSFs) or other light guides.

The scintillator volume can be in a tubular form, such as the form described in connection with FIG. 15, for example. The entrance and exit surfaces can be outer and inner curved surfaces, respectively, of a tubular wall of the scintillator volume if the volume defines an inner hollow portion. The first and second pluralities of light guides can be first and second pluralities of ribbons of WSFs, respectively, covering the outer and inner curved surfaces, respectively, of the tubular wall. The first plurality of ribbons can be wrapped around the outer curved surface in a spatially periodic, substantially helical pattern. The second plurality of ribbons can be inlaid around and adjacent to the inner curved surface in a repeating, spatially periodic, substantially helical pattern.

The at least one first photodetector and the at least one second photodetector can be photomultiplier tubes (PMTs).

The at least one first photodetector and the at least one second photodetector can be separate anodes of at least one multi-anode PMT.

A scintillator material of the scintillator volume can include one or more materials selected from a group consisting of BaFCl, GOS, YOS, and ZnS.

FIG. 23 is a cross-sectional view of an advantageous embodiment configured specifically for x-ray transmission imaging. One volume of scintillator 2274 is advantageously used for both the low-energy detector channel 2280 and the high-energy channel 2282. The low-energy x-rays are preferentially absorbed closer to the entrance surface 2276 of the scintillator volume 2274, with the resulting scintillation light preferentially entering the layer of WSF 2280 optically coupled to the entrance surface 2274 of the scintillator volume. The higher-energy x-rays, which are more penetrating, will be absorbed, on average, deeper in the scintillator medium volume 2274, and the resulting scintillation light will preferentially enter the HE layer of WSF 2282 optically coupled to the exit surface 2278 of the scintillator volume 2274.

A reflector 2296 (top) assists to optically couple scintillation light produced by lower-energy x-rays by reflecting such light back toward the layer 2280. Similarly, a reflector 2296 (bottom) assists to optically couple scintillation light produced by higher-energy x-rays by reflecting such light back toward the layer 2282.

Figures 24, 25:
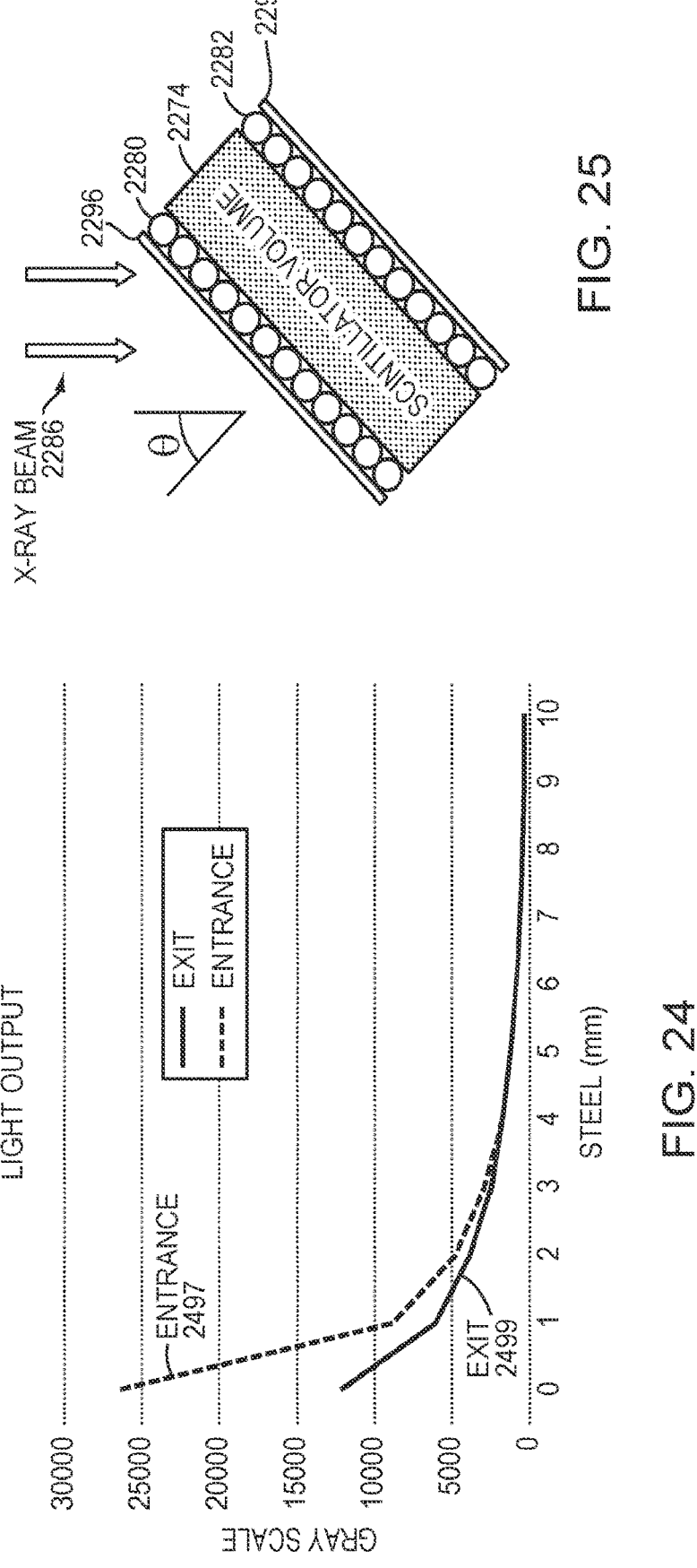
FIG. 24 is a graph illustrating simulated relative light output from a 500 mg/cm$^2$ volume of BaFCl with WSF layers on the entrance and exit surfaces.
FIG. 25 is cross-sectional view illustration of certain components of an embodiment detector system, tilted with respect to the incident x-ray beam to increase detection efficiency.
Figure 26:
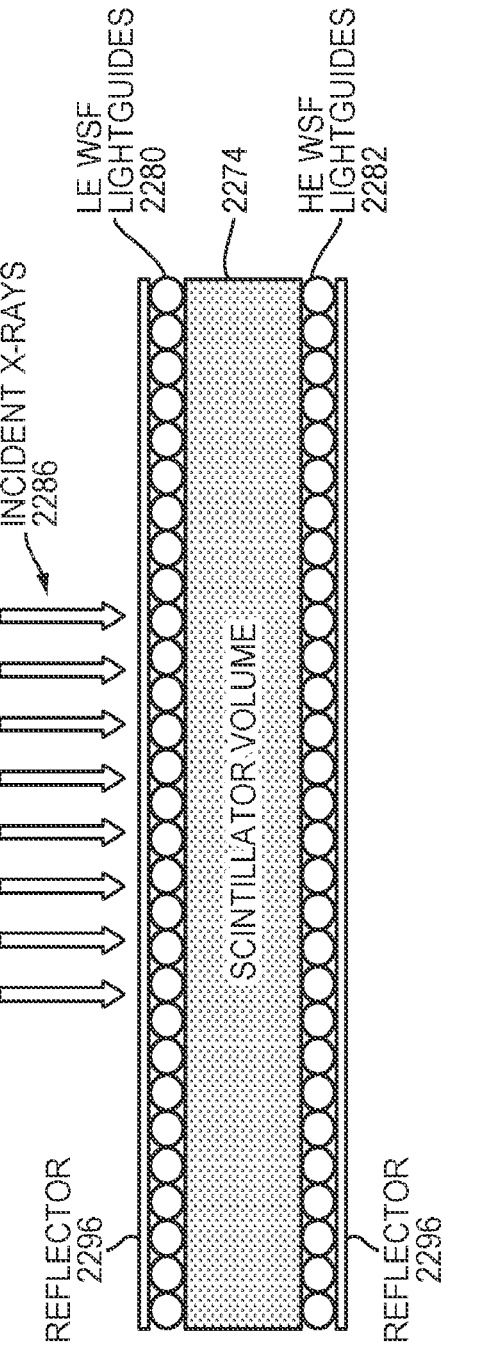
FIG. 26 is a cross-sectional view illustration of certain components of an embodiment detector system optimized for area detection such as use in backscatter imaging.

The energy discrimination characteristics of the detector system shown in FIG. 22, and the detector structures of FIGS. 23, 25, and 26, for example, can be optimized by carefully selecting the scintillator medium according to the following criteria:

Scintillator medium composition

Scintillator thickness

Scintillator optical attenuation

The scintillator medium and thickness can be carefully selected to ensure that the detection efficiency of the high-energy x-rays is high, while ensuring that the mean absorption depth of the x-rays in the low-energy and high-energy regions are well separated, providing good discrimination in the amount of scintillation light collected in the two independent WSF layers. This can be further enhanced by ensuring that the mean-free-path of the scintillation light in the scintillation medium is relatively short. This ensures that the light from the low-energy x-rays (absorbed near the entrance surface) has a low probability of being absorbed in the WSF layer on the exit surface, and conversely, that the light from the higher-energy x-rays (absorbed closer to the exit surface) has a lower probability of being absorbed in the WSF layer on the entrance surface.

A preferred scintillator medium that is relatively low cost and easy to incorporate mechanically into larger detectors is scintillating phosphor screen, such as BaFCl. This particular phosphor has a peak scintillation wavelength of about 390 nm, which is ideally matched to the peak absorption spectra of many types of WSF. It has a high detection efficiency for x-rays in the energy range of 25 keV to 225 keV and because of its crystalline structure, it has a relatively short mean-free-path of less than a millimeter for self-absorption of its own scintillation light, enhancing the separation in light collection between the two layers of WSF for low-energy versus high-energy x-rays.

By optimizing the thickness and optical light attenuation characteristics of the scintillator medium, a "dead" zone at the center of the scintillator volume can be established, for which scintillation light cannot reach either layer of WSF. The scintillator material in this center zone is therefore now acting effectively as the filter shown at the center of the prior-art detector in FIG. 19, as light from this region is not able to be detected at all. The only effect of this center material is to absorb or filter the higher energy x-rays that can pass into the high-energy region of the scintillator and contribute to the HE channel signal. This "dead" zone can therefore be optimized to further enhance the energy discrimination capability of the detector, much as the filter in FIG. 19 is designed to do.

Tests were performed with a 500 mg/cm2 thick volume of BaFCl phosphor screen as a scintillator volume sandwiched between two layers of WSFs. The phosphor screen had a transparent backing so that scintillation light could escape from both the entrance and exit surfaces of the scintillator. The light output of each WSF layer was recorded using an incident 140 kV x-ray beam, as different thicknesses of steel were introduced between the x-ray source and the detector.

FIG. 24 is a graph illustrating results from the simulation. It can be seen that as more steel is added, the signal from the entrance WSF layer falls off much more rapidly than the signal from the exit WSF layer, indicating that the entrance layer WSF is preferentially detecting scintillation light from the lower-energy x-rays compared with the exit WSF layer.

Those skilled in the art will understand in view of this disclosure that such a detector is then able to provide the operator with material discrimination. X-rays transmitted though high-Z materials such as steel have fewer low-energy x-rays remaining in the beam than x-rays passing through organic materials, such as water or plastic. By analyzing the relative ratio of detector signals from the low and high energy channels, material discrimination can be performed. This is typically indicated to the operator by applying a color pallet to the image: orange for organic materials with low effective atomic number (Z), green for intermediate-Z materials such as Al, and blue for higher-Z materials such as steel. Thus, the characteristic 2296 of the incident x-rays described above may include the relative ratio of detector signals from the lower- and higher-energy channels, an indication of a likely material or material class of the target, or an indication such as a color display indicating a likely range of atomic number (Z) of a target, as indicated by analyzing energy of the incident x-rays.

Thickness of a scintillator volume may be further optimized as follows, and Table 1 will aid in the description.

TABLE 1

| keV | MFP (mm) | | 86% Areal Density (mg/cm2)* | |
|---|---|---|---|---|
| | GdOS | BaFCl | GdOS | BaFCl |
| 50 | 0.1 | 0.4 | 21 | 32 |
| 120 | 0.9 | 3.0 | 158 | 248 |
| 140 | 1.3 | 4.4 | 233 | 361 |
| 160 | 1.9 | 5.9 | 321 | 492 |
| 220 | 3.8 | 11.5 | 657 | 948 |
| 600 | 16.4 | 39.0 | 2847 | 3233 |

*15 degree incidence angle

The first two columns of Table 1 above show the mean free path of x-rays of various energies in two different common scintillator screen materials. This is equivalent to the thickness required, assuming direct illumination (90 degree incidence angle), to stop 63% of the x-rays at the given energy.

The third and fourth columns of Table 1 show the areal density of scintillator screen needed to stop 63% of the incident x-rays, when the screen is angled at 15 degrees to the incident beam. Note that the lowest energy x-rays (E<50 keV) are absorbed within the first 0.1 and 0.4 mm of scintillator screen for GdOS and BaFCl, respectively.

If a low energy bin is defined as E(LE)<120 keV, then the low energy x-rays are mostly absorbed in the first 158 mg/cm2 and 248 mg/cm2 of the screen. If a 500 mg/cm2 thick screen is used, this will provide adequate separation between the low energy (E<120 keV) and higher energy (E>120 keV) x-rays.

FIG. 25 illustrates enhancement of detection efficiency by orienting the detector. For transmission imaging, the detection efficiency of the detector of FIG. 23 can be enhanced by orienting the detector scintillator volume 2274 so that it is illuminated obliquely by the incident x-ray beam 2286. This increases the effective length of the path that the incident x-ray beam must travel though the scintillator medium, increasing the probability of absorption of the x-rays in the medium, and increasing the probability of detection. Note that this requires no additional scintillator material, and therefore provides a very cost-effective way of improving detection efficiency. By orienting the entrance surface with a normal to the entrance surface at a non-zero angle θ with respect to the x-ray beam 2286, an effective thickness of the scintillator volume is increased by the factor 1/cos(θ). For example, by tilting the detector at a 75° angle to the incident beam, the detection efficiency of the scintillator is increased by almost a factor of four.

A further embodiment of the detector optimized for backscatter imaging is shown in FIG. 26. It is similar to the transmission detector configuration of FIG. 23, except that FIG. 26 is an area detector optimized for detecting diffuse scattered x-rays over a larger area rather than a strip detector optimized for detecting transmitted x-rays in an incident beam. In this configuration, the scintillator volume 2274 is formed of a sheet (or plate) of scintillator medium, and the layers of WSF 2280, 2282 consist of multiple ribbons placed side-by-side to one another.

Increasing Detector Resolution of Dual-Energy Embodiments

Described herein in connection with FIGS. 1 and 6-18 are various embodiments of transmission detectors utilizing WSF that exhibit increased imaging resolution. Since the detector embodiments described in connection with FIGS. 22-26 can use similar ribbons of WSF in some embodiments, it will become apparent to those skilled in the art, in reference to this disclosure, that features described in connection with FIGS. 1 and 6-18 can be incorporated into embodiments described in connection with FIGS. 22-26, and vice-versa.

In some embodiments, various aspects of embodiments may be implemented in computers or software or firmware program products. In one example, lookup tables may be run in software or firmware. The computer program product(s) may be stored on a non-transitory computer readable medium that includes computer readable instructions that cause one or more processors to execute aspects of embodiment systems or related methods.

The teachings of any patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A detector system for detecting a scanning beam of x-rays, the detector system comprising:

one or more scintillator volumes configured to be oriented along a scan axis of a scanning beam of x-rays to receive x-rays from the scanning beam transmitted through a target, the one or more scintillator volumes further configured to produce scintillation photons responsive to receiving the x-rays;

a plurality of ribbons of wavelength-shifting fibers (WSFs) optically coupled to the one or more scintillator volumes along the scan axis via a spatial periodic adjacency of the plurality of ribbons to the scan axis, the plurality of ribbons configured to receive scintillation photons from the one or more scintillator volumes via the spatial periodic adjacency as the scanning beam of x-rays scans over the scan axis;

at least one respective photodetector coupled to an end of each respective ribbon of the plurality of ribbons, each respective photodetector configured to detect the scintillation photons carried by the respective ribbon and to produce a respective signal responsively; and a signal combiner configured to reference a calibration to combine, selectively, respective signals from one or more ribbons of the plurality of ribbons, for positions of the scanning beam along the scan axis, to create a combined signal representing a scan of the target with enhanced spatial resolution along the scan axis.

2. The detector system of claim 1, further comprising a processor configured to create an image from the combined signal.

3. The detector system of claim 1, wherein the signal combiner is configured to reference one or more predefined lookup tables to combine the signals from the one or more ribbons for the positions of the scanning beam.

4. The detector system of claim 1, wherein a first ribbon and a second ribbon of the plurality of ribbons are a low-energy channel and a high-energy channel, respectively, configured to receive scintillation photons produced by relatively lower-energy x-rays and relatively higher-energy x-rays, respectively, interacting with the one or more scintillator volumes, and wherein scintillation photons carried by the high-energy channel represent x-rays of higher average energy than scintillation photons carried by the low-energy channel.

5. The detector system of claim 4, wherein the one or more scintillator volumes comprise a single scintillator volume that produces scintillation photons carried by both the low-and high-energy channels.

6. The detector system of claim 4, wherein the one or more scintillator volumes comprise first and second scintillator volumes that produce scintillation photons carried by the low-and high-energy channels, respectively.

7. A detector system for determining a characteristic of an energy spectrum of x-rays, the detector system comprising:

a scintillator volume having an entrance surface and an exit surface, the entrance surface configured to receive incident x-rays, the scintillator volume configured to emit scintillation light responsive to the incident x-rays, and the exit surface configured to pass a portion of the incident x-rays that traverse a thickness of the scintillator volume between the entrance surface and the exit surface, the thickness of the scintillator volume being larger than a self-attenuation length of a scintillator material of the scintillator volume;

a first plurality of light guides optically coupled to the entrance surface of the scintillator volume;

a second plurality of light guides optically coupled to the exit surface of the scintillator volume;

at least one first photodetector optically coupled to an end of the first plurality of light guides and configured to output a first signal responsive to scintillation light from the scintillator volume;

at least one second photodetector optically coupled to an end of the second plurality of light guides and configured to output a second signal responsive to scintillation light from the scintillator volume; and a spectrum analyzer configured to receive the first and second signals responsive to the scintillation light from the scintillator volume and to determine a characteristic of an energy spectrum of the incident x-rays based on the first and second signals.

8. The detector system of claim 7, wherein the scintillator volume is a strip scintillator volume configured to receive the incident x-rays at the entrance surface thereof, from a sweeping x-ray beam transmitted through a target, over a sweep of the sweeping x-ray beam.

9. The detector system any of claim 7, wherein the scintillator volume is an area scintillator volume configured to receive the incident x-rays at the entrance surface via x-ray scattering from a target.

10. The detector system of claim 7, wherein the scintillator volume is an area scintillator volume and the incident x-rays are received at the entrance surface via passive emission from a target.

11. The detector system of claim 7, wherein the first and second pluralities of light guides are wavelength-shifting fibers (WSFs).

12. The detector system of claim 7, wherein the scintillator volume is in a tubular form, and wherein the entrance and exit surfaces are outer and inner curved surfaces, respectively, of a tubular wall of the scintillator volume.

13. The detector system of claim 12, wherein the first and second pluralities of light guides are first and second pluralities of ribbons of WSFs, respectively, covering the outer and inner curved surfaces, respectively, of the tubular wall.

14. The detector system of claim 13, wherein the first plurality of ribbons are wrapped around the outer curved surface in a spatially periodic, substantially helical pattern.

15. The detector system of claim 14, wherein the second plurality of ribbons are inlaid around the inner curved surface in a spatially periodic, substantially helical pattern.

16. The detector system of claim 7, wherein the at least one first photodetector and the at least one second photodetector are photomultiplier tubes (PMTs).

17. The detector system of claim 7, wherein the at least one first photodetector and the at least one second photodetector are separate anodes of at least one multi-anode PMT.

18. The detector system of claim 7, wherein the scintillator material of the scintillator volume comprises one material.

19. The detector system of claim 18, wherein the one material is selected from the group consisting of BaFCl, GOS, YOS, and ZnS.

20. The detector system of claim 7, wherein the spectrum analyzer is further configured to output the characteristic of the energy spectrum.

21. The detector system of claim 7, wherein the scintillator material of the scintillator volume comprises a plurality of materials.

22. The detector system of claim 21, wherein the plurality of materials is selected from the group consisting of BaFCl, GOS, YOS, and ZnS.

* * * * *